US008414899B2

(12) United States Patent
Cohen et al.

(10) Patent No.: US 8,414,899 B2
(45) Date of Patent: Apr. 9, 2013

(54) VACCINES COMPRISING MULTIMERIC HSP60 PEPTIDE CARRIERS

(75) Inventors: Irun R. Cohen, Rehovot (IL); Hila Amir-Kroll, Gedera (IL); Noam Cohen, Rishon le Zion (IL); Gabriel Nussbaum, Jerusalem (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 12/296,428

(22) PCT Filed: Apr. 11, 2007

(86) PCT No.: PCT/IL2007/000468
§ 371 (c)(1),
(2), (4) Date: Dec. 16, 2008

(87) PCT Pub. No.: WO2007/116409
PCT Pub. Date: Oct. 18, 2007

(65) Prior Publication Data
US 2009/0269370 A1 Oct. 29, 2009

Related U.S. Application Data

(60) Provisional application No. 60/790,782, filed on Apr. 11, 2006.

(51) Int. Cl.
A61K 39/00 (2006.01)
A61K 39/02 (2006.01)
A61K 39/385 (2006.01)
A61K 39/295 (2006.01)
A61K 45/00 (2006.01)
A61K 47/00 (2006.01)

(52) U.S. Cl. ............ 424/197.11; 424/184.1; 424/185.1; 424/193.1; 424/202.1; 424/203.1; 424/234.1; 424/278.1

(58) Field of Classification Search .................. None
See application file for complete search history.

(56) References Cited

U.S. PATENT DOCUMENTS

| | | | |
|---|---|---|---|
| 4,073,943 A | 2/1978 | Wretlind | |
| 4,168,308 A | 9/1979 | Wretlind | |
| 5,154,923 A | 10/1992 | Van Eden | |
| 5,229,490 A | 7/1993 | Tam | |
| 5,425,946 A | 6/1995 | Tai | |
| 5,565,204 A | 10/1996 | Kuo | |
| 5,597,572 A | 1/1997 | Huergo | |
| 5,736,146 A * | 4/1998 | Cohen et al. ............ | 424/197.11 |
| 5,773,007 A | 6/1998 | Penney | |
| 5,869,058 A * | 2/1999 | Cohen et al. ............ | 424/194.1 |
| 5,961,970 A | 10/1999 | Lowell | |
| 6,080,589 A | 6/2000 | Kandil | |
| 6,350,449 B1 | 2/2002 | Jennings | |
| 6,642,354 B2 | 11/2003 | Granoff | |
| 6,656,472 B1 | 12/2003 | Chong | |
| 6,855,321 B1 * | 2/2005 | Rappuoli et al. ............ | 424/192.1 |
| 6,936,261 B2 | 8/2005 | Granoff | |
| 7,018,637 B2 * | 3/2006 | Chong et al. ............ | 424/197.11 |
| 7,157,089 B1 | 1/2007 | Mizzen | |
| 2008/0279878 A1 * | 11/2008 | Cohen et al. ............ | 424/186.1 |
| 2009/0004218 A1 * | 1/2009 | Hacohen et al. ............ | 424/193.1 |
| 2009/0269370 A1 * | 10/2009 | Cohen et al. ............ | 424/197.11 |
| 2010/0003225 A1 * | 1/2010 | Cohen et al. ............ | 424/93.21 |

FOREIGN PATENT DOCUMENTS

| | | | |
|---|---|---|---|
| WO | WO 93/17712 | * | 9/1993 |
| WO | 94/02156 | | 2/1994 |
| WO | WO 94/03208 A1 | * | 2/1994 |
| WO | 94/29459 | | 12/1994 |
| WO | 95/24923 | | 9/1995 |
| WO | 95/34638 | | 12/1995 |
| WO | 97/06821 | | 2/1997 |
| WO | 97/22349 | | 6/1997 |
| WO | 98/01538 | | 1/1998 |
| WO | 90/10449 | | 9/1999 |
| WO | WO 99/55730 A2 | * | 11/1999 |
| WO | 01/09298 | | 2/2001 |
| WO | 01/47552 | | 7/2001 |
| WO | 02/058737 | | 8/2002 |
| WO | WO 2004/041157 A2 | * | 5/2004 |
| WO | 2004/103400 | | 12/2004 |
| WO | 2005/000345 | | 1/2005 |
| WO | 2005/004909 | | 1/2005 |
| WO | WO 2005/002453 | * | 1/2005 |
| WO | WO 2005/093524 | * | 9/2005 |
| WO | WO 2006/097914 A2 | * | 9/2006 |
| WO | WO 2007/116409 A2 | * | 10/2007 |
| WO | WO 2009/090650 A2 | * | 7/2009 |

OTHER PUBLICATIONS

Amir-Kroll et al (The Journal of Immunology, 170:6165,6171, 2003).*
Konen-Waisman et al (The Journal of Immunology, 154:5977-5985, 1995).*
Morand et al, J. Clin. Microbiol. 2009, 47:2489-2495.*
Amir-Kroll et al, Vaccine, 2006, 24:6555-6563.*
Konen-Waisman et al, J. Immunol., 1995, 154:5977-5985.*
Amir-Kroll et al, J. Immunol., 2003, 170:6165-6171.*
Konen-Waisman et al, J. Infectious Diseases, 1999, 179:403-413.*
AlonsoDeVelasco et al., "*Streptococcus pneumoniae*: Virulence Factors, Pathogenesis, and Vaccines", Microbiol Rev, 59:591-603 (Dec. 1995).

(Continued)

*Primary Examiner* — Nita M Minnifield
(74) *Attorney, Agent, or Firm* — Rodney J. Fuller; Booth Udall Fuller, PLC

(57) ABSTRACT

The present invention provides improved vaccine compositions having enhanced immunogenicity and methods of using same. The compositions and methods include immunogenic conjugates containing peptide carriers derived from heat shock protein 60 (HSP60). The known synthetic peptide carrier, p458, provides significantly improved immunogenicity when provided as a multimeric conjugate comprising a plurality of peptide carrier units conjugated to each antigen. Cell vaccine compositions comprising antigen presenting cells loaded with multimeric p458 conjugates are also provided.

26 Claims, 13 Drawing Sheets

OTHER PUBLICATIONS

Figure 1A:
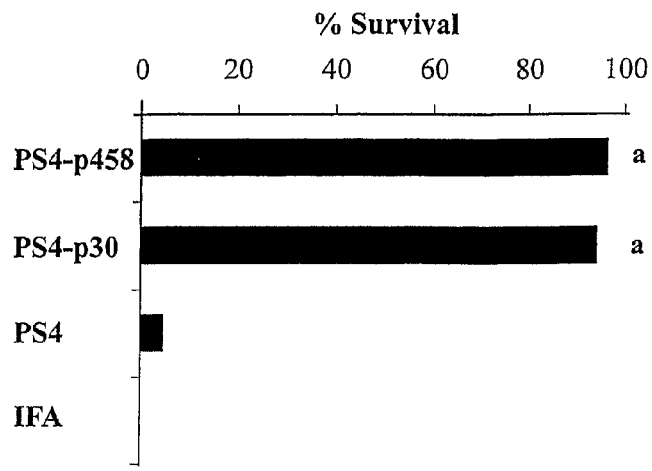

Barrios et al., "Mycobacterial heat-shock proteins as carrier molecules. II: The use of the 70-kDa mycobacterial heat-shock protein as carrier for conjugated vaccines can circumvent the need for adjuvants and *Bacillus calmette* Guerin priming", Eur S of Immuol, 22:1365-1372 (1992).

Bartoloni A. et al., "Immunogenicity of meningococcal B polysaccharide conjugated to tetanus toxoid or CRM197 via adipic acid dihydrazide", Vaccine 13(5):463-470 (1995).

Burnie J.P. et al., "Identification of an Immunodominant ABC Transporter in Methicillin-Resistant *Staphylococcus aureus* Infections", Infect Immun. 68(6):3200-3209 (Jun. 2000).

Carlin N. I. et al., "Monoclonal Antibodies Specific for Shigella flexneri Lipopolysaccharides: Clones Binding to Type IV, V, and VI Antigens, Group 3,4 Antigen, and an Epitope Common to All Shigella Flexneri and Shigella dysenteriae Type 1 Strains", Infect Immun. 55(6):1412-1420 (Jun. 1987).

Cohen-Sfady M. et al., "Heat Shock Protein 60 Activates B Cells via the TLR4-MyD88 Pathway", J Immunol, 175:3594-3602 (2005).

Devi S. J. et al., "Preclinical Evaulation of Group B Neisseria meningitidis and *Escherichia coli* K92 Capsular Polysaccharide-Protein Conjugate Vaccines in Juvenile Rhesus Monkeys", Infect Immun, 65(3):1045-1052 (Mar. 1997).

Fainaru O. et al., "Runx3 regulates mouse TGF-B-mediated dendritic cell function and its absence results in airway inflammation", EMBO J., 23(4):969-979 (2004).

Feng L. et al., "Strutural and genetic evidence that the *Escherichia coli* 148 O antigen is the precursor of the shigella dysenteriae type 1 O antigen and identification of a glucosyltransferase gene", Microbiology, 153:139-147 (2007).

Finne J. et al., "Antigenic Similarities Between Brain Components and Bacteria Causing Meningitis", Lancet, 8346:355-357 (Aug. 13, 1983).

Friedl P. et al., "Collective cell migration in morphogenesis and cancer", Int J Dev Biol, 48:441-449 (2004).

Fukuda M., "Possible Roles of Tumor-associated Carbohydrate Antigens", Cancer Res, 56(10):2237-2244 (May 15, 1996).

Fusco P. C. et al., "Preclinical Evaluation of a Novel Group B Meningococcal Conjugate Vaccine that Elicits Bactericidal Activity in both Mice and Nonhuman Primates", J Infect Dis, 175(2):364-372 (1997).

Goldblatt D., "Conjugate vaccines", Clin Exp Immunol, 119(1):1-3 (2000).

Gotschlich E. C., "Development of Polysaccharide Vaccines for the Prevention of Meningococcal Diseases", Monogr Allergy 9:245-258 (1975).

Haneberg B. et al., "Intranasal Administration of a Meningococcal Outer Membrane Vesicle Vaccine Induces Persistent Local Mucosal Antibodies and Serum Antibodies with Strong Bactericidal Activity in Humans", Infect Immun, 66(4):1334-1341 (Apr. 1998).

Henikoff S. et al., "Amino acid substitution matrices from protein blocks", Proc Natl Acad Sci U S A., 89(22):10915-10919 (Nov. 1992).

Kohn, J. et al., "A New Approach (Cyano-Transfer) for Cyanogen Bromide Activation of Sepharose at Neutral pH, Which Yields Activated Resins, Free of Interfering Nitrogen Derivatives", Biochem Biophys Res Commun, 107(3):878-884 (Aug. 16, 1982).

Komminoth P. et al., "Polysialic Acid of the Neural Cell Adhesion Molecule in the Human Thyroid: A Marker for Medullary Thyroid Carcinoma and Primary C-Cell Hyperplasia", Am J Surg Pathol, 18(4):399-411 (1994).

Konen-Waisman S. et al., "Self Heat-Shock Protein (hsp60) Peptide Serves in a Conjugate Vaccine against a Lethal Pneumococcal Infection", J Infect Dis, 179(2):403-413 (1999).

Krug, L. M. et al., "Vaccination of Small Cell Lung Cancer Patients with Polysialic Acid or N-Propionylated Polysialic Acid Conjugated to Keyhold Limpet Hemocyanin", Clin Cancer Res., 10(3):916-923 (Feb. 1, 2004).

Lesinski, G. B. et al., "Novel vaccine strategies to T-independent antigens", J Microbiol Methods, 47:135-149 (2001).

Lifely, M. R. et al., "An integrated molecular and immunological approach towards a meningococcal group B vaccine", Vaccine, 5(1):11-26 (Mar. 1987).

Lindberg, A. A., "Glycoprotein conjugate vaccines", Vaccine, 17:S28-S36 (1999).

Lussow, A. R. et al., "Towards vaccine optimisation", Immunol Letters, 25:255-264 (1990).

Lussow, A. R. et al., "Mycobacterial heat-shock proteins as carrier molecules", Eur. J. Immunol, 21:2297-2302 (1991).

Miller, E. et al., "Planning, registration, and implementation of an immunisation campaign against meningococcal serogroup C disease in the UK: a success story", Vaccine, 20:S58-S67 (2002).

Morley, S. L. et al., "Immunogenicity of a serogroup B meningococcal vaccine against multiple Neisseria meningitidis strains in infants", Pediatr Infect Dis J, 20(11):1054-1061 (Nov. 2001).

Perkins, B. A. et al., "Immunogenicity of Two Efficacious Outer Membrane Protein-Based Serogroup B Meningococcal Vaccines among Young Adults in Iceland", J Infect Dis, 177(3):683-691 (1998).

Pizza, M. et al., "Identification of Vaccine Candidates Against Serogroup B Meningococcus by Whole-Genome Sequencing", Science, 287:1816-1820 (2000).

Qu, B. et al., "Poly(a2,8-deaminoneuraminic acid) is expressed in lung on a single 150-kDa glycoprotein and is an oncodevelopmental antigen", Proc Natl Acad Sci U S A, 93(17):8995-8998 (Aug. 1996).

Rappuoli, R., "Conjugates and reverse vaccinology to eliminate bacterial meningitis", Vaccine, 19:2319-2322 (2001).

Richmond, P. et al., "Ability of 3 Different Meningococcal C Conjugate Vaccines to Induce Immunologic Memory after a Single Dose in UK Toddlers", J Infect Dis, 183:160-163 (2001).

Robbins, J.B. et al., "Planning for a Second (23 Valent) Generation Pneumococcal Vaccine", Bull Eur Physiopathol Respir, 19:215-226 (1983).

Robertson, S. E. et al., "The WHO Vaccine Trial Registry", Vaccine, 20:31-41 (2002).

Rouvio, O. et al., "Self HSP60 peptide serves as an immunogenic carrier for a CTL epitope against persistence of murine cytomegalovirus in the salivary gland", Vaccine, 23:3508-3518 (2005).

Schneerson, R. et al., "Preparation, Characterization, and Immunogenicity of Haemophilus Influenzae Type b Polysaccharide-Protein Conjugates", J Exp Med, 152:361-376 (1980).

Trotter, C. L. et al., "Effectiveness of meningococcal serogroup C conjugate vaccine 4 years after introduction", Lancet, 364:365-367 (Jul. 24, 2004).

Vinogradov, E. et al., "Structures of Lipopolysaccharides from Klebsella pneumoniae", J Biol Chem, 277(28):25070-25081 (Jul. 12, 2002).

Von Eiff, C. et al., "Distribution of capsular and surface polysaccharide serotypes of *Staphylococcus aureus*", Diagn Microbiol Infect Dis, 58(3):297-302 (2007).

Cohen, Noam et al., "Pneumoccal Capsular Polysaccharide Is Immunogenic When Present on the Surface of Macrophages and Dendritic Cells: TLR4 Signaling Induced by a Conjugate Vaccine or by Lipopolysaccharide Is Conducive", The Journal of Immunology, 180:2409-2418 (2008).

* cited by examiner

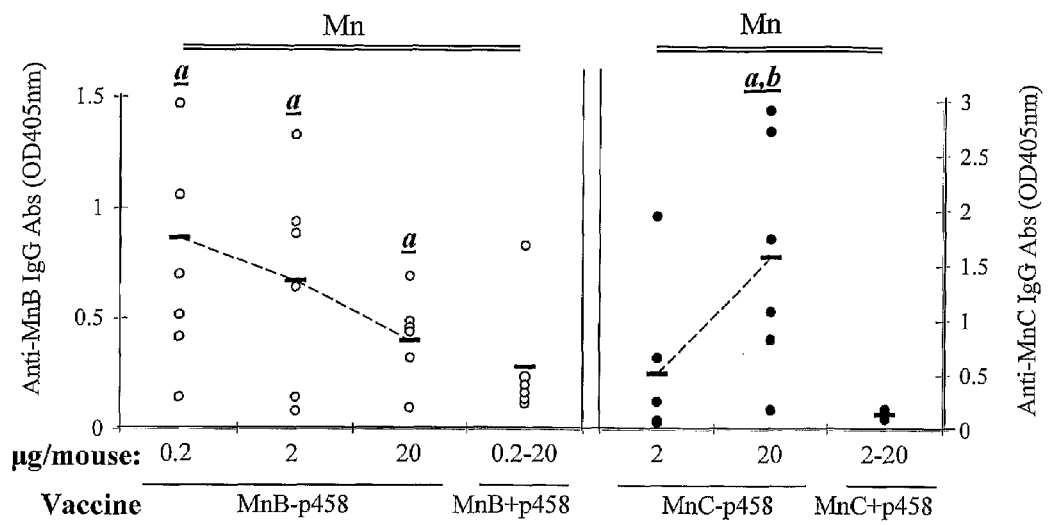
Figure 9A                           Figure 9B
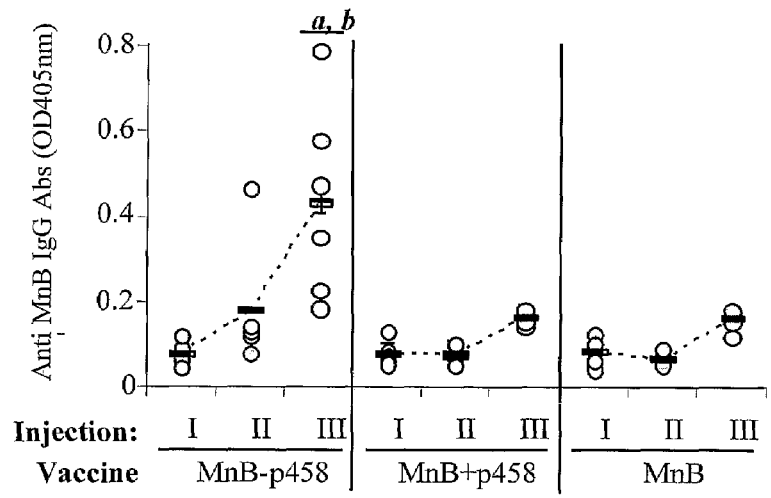
Figure 10

VACCINES COMPRISING MULTIMERIC HSP60 PEPTIDE CARRIERS

RELATED APPLICATION DATA

This application is the U.S. national stage of PCT/IL2007/000468 filed on Apr. 11, 2007, which is based on and claims the benefit of U.S. Provisional Application No. 60/790,782 filed on Apr. 11, 2006, the content of each of which is expressly incorporated herein in its entirety by reference hereto.

FIELD OF THE INVENTION

The present invention is directed to improved vaccine compositions having enhanced immunogenicity and to methods of using same, the compositions comprising antigens and peptide carriers derived from heat shock protein 60 (HSP60).

BACKGROUND OF THE INVENTION

Effective vaccines, particularly vaccines against bacterial capsular polysaccharide (CPS) antigens, appear to require three components: (i) a CPS B-cell epitope to induce the production of antibody (Ab) that mediates opsonin-dependent phagocytosis and bacterial clearance; (ii) a T-cell epitope to induce an IgG isotype switch and immune memory; and (iii) an adjuvant to induce innate-cell receptor activation of a pro-inflammatory cytokine environment. Classical adjuvants contain bacterial or other ligands that stimulate Toll-like receptor (TLR) signaling of innate immune cells. Stimulation of TLR signaling enhances the production of pro-inflammatory cytokines and the up-regulation of MHC and co-stimulatory molecules. Thus, TLR stimulation plays a key role in the interface between innate and adaptive immunity. Indeed, TLR molecules are considered to be "adjuvant receptors", and the ligands that activate them are "adjuvants". Vaccines that incorporate ligands for TLR stimulation were shown to boost vaccine responses.

Heat Shock Protein 60 (HSP60)

HSP60 belongs to a family of chaperone molecules highly conserved throughout evolution; a similar HSP60 molecule is present in all cells, prokaryotes and eukaryotes. The human HSP60 molecule was formerly designated HSP65, but is now designated HSP60 in view of more accurate molecular weight information; by either designation, the protein is the same. Mammalian HSP60 is highly homologous to the bacterial cognates, showing about 50% amino acid identity. Thus, HSP60 is shared by the host and its parasites, and is immunogenic, cross-reactive, and universally expressed in inflammation. Furthermore, HSP60 is well recognized by the immune system and is a part of the set of self-molecules for which autoimmunity naturally exists; HSP60 is member of the immunologic homunculus. Heat shock, IFNγ, bacterial or viral infection, and inflammation, all result in the presentation of endogenous HSP60 epitopes on MHC class II molecules leading to the activation of HSP60-specific T cells, even in healthy individuals.

U.S. Pat. No. 7,157,089 discloses fusion proteins comprising influenza virus antigens and stress proteins useful for vaccination against influenza infection. U.S. Pat. No. 7,157,089 does not disclose conjugates comprising any specific peptide carrier derived from heat shock proteins such as HSP60.

WO 94/29459 to Young is directed to a fusion protein wherein a stress protein is fused to an antigen protein, particularly a fusion protein that contains a HSP70 and an HIV antigen.

WO 95/24923 to Srivastava et al. discloses complexes of stress proteins noncovalently associated with peptides. WO 95/24923 does not teach or suggest complexes comprising multimeric HSP60-derived peptide carriers.

WO 97/06821 to Rothman et al. relates to methods and compositions for inducing an immune response in a subject, wherein at least one heat shock protein in combination with one or more defined target antigens is administered to the subject. Particularly, WO 97/06821 discloses complexes of HSP70 and peptide antigens.

European Patent EP 262 710 and U.S. Pat. No. 5,154,923 to Van Eden et al. describe peptides having an amino acid sequence corresponding to positions 171-240 and 172-192, respectively, of a *Mycobacterium boris* BCG 64 kD polypeptide, that are useful as immunogens inducing resistance to autoimmune arthritis and similar autoimmune diseases.

PCT Pub. No. WO 90/10449 to some of the inventors of the present invention describes a peptide designated p277 having an amino acid sequence corresponding to positions 437-460 of the human HSP65 molecule that is useful as immunogen inducing resistance to insulin dependent diabetes mellitus (IDDM). A control peptide, designated p278, corresponding to positions 458-474 of human HSP65, did not induce resistance to IDDM.

Lussow et al. (1990) showed that the priming of mice with live *Mycobacterium tuberculosis* var. *bovis* (BCG) and immunization with the repetitive malaria synthetic peptide (NANP)40 conjugated to purified protein derivative (PPD), led to the induction of high and long-lasting titers of anti-peptide IgG antibodies. Later on, Lussow et al. (1991) showed that mycobacterial HSPs of 65 kDa (GroEL-type) and 70 kDa (DnaK-type) acted as carrier molecules in mice, previously primed with BCG, for the induction of high and long-lasting titers of IgG against the repetitive malaria synthetic peptide (NANP)40.

Barrios et al. (1992) have shown that mice immunized with peptides or oligosaccharides conjugated to the Mycobacterial 70 kDa HSP produced high titers of IgG antibodies in the absence of any previous priming with BCG. This adjuvant-free carrier effect of the 70 kDa HSP was T cell dependent, since no anti-peptide or anti-70 kDa IgG antibodies were induced in athymic nu/nu mice. In addition, preimmunization with the 65 kDa HSP could substitute for BCG in providing effective priming for the induction of anti-(NANP)40 antibodies. Finally, both the 65 kDa and 70 kDa Mycobacterial HSP acted as carrier molecules for the induction of IgG antibodies to group C meningococcal oligosaccharides, in the absence of adjuvants.

Peptide p458 (corresponding to positions 458-474 and 437-453 of mammalian HSP60) was previously used to develop conjugate vaccines to *Streptococcus pneumoniae*, *Salmonella typhi* (then named CP1) and to a murine cytomegalovirus CTL-epitope (Amir-Kroll et al., 2003; Konen-Waisman et al., 1999; Konen-Waisman et al., 1995; Rouvio et al., 2005).

U.S. Pat. No. 5,736,146 to some of the inventors of the present invention discloses conjugates of poorly immunogenic antigens with a synthetic peptide carrier comprising a T cell epitope derived from the sequence of human heat shock protein HSP65, or an analog thereof, said peptide or analog being capable of increasing substantially the immunogenicity of the antigen. The '146 patent discloses conjugates of a peptide corresponding to positions 458-474 and 437-453 of human or mouse HSP60 and homologs thereof with a wide variety of antigens including peptides, proteins and polysaccharides such as bacterial polysaccharide (e.g. capsular polysaccharide (CPS) Vi of *Salmonella typhi*), and antigens derived from HIV virus or from malaria antigen.

U.S. Pat. No. 5,869,058 to some of the inventors of the present invention discloses conjugates of poorly immunogenic antigens, e.g., peptides, proteins and polysaccharides, with a synthetic peptide carrier comprising a T cell epitope derived from the sequence of *E. coli* HSP65 (GroEL), or an analog thereof, said peptide or analog being capable of increasing substantially the immunogenicity of the antigen. A suitable peptide according to the invention is Pep278e, which corresponds to positions 437-453 of the *E. coli* HSP65 molecule.

*Neisseria meningitidis* (*N. meningitidis*, meningococcus, Mn) and *Streptococcus pneumoniae* (*S. pneumoniae*, pneumococcus, Pn) are major causes of bacterial meningitis and pneumonia throughout the world, particularly in children. Thus, developing vaccines conferring immunity against these pathogens has been the focus of extensive research efforts.

Meningococcal Vaccines

The Meningococcal type B capsular polysaccharide (MnB), like other CPS, is a T-independent (TI) antigen. TI antigens are not recognized by helper T cells and so activate only B cells leading predominantly to a short-lived IgM response and to almost no immunological memory. Protein carriers have been conjugated to TI antigens to recruit T-cell help to induce B-cells to switch to IgG secretion and to generate immunological memory (Goldblatt et al., 2000). Indeed, an immunogenic carrier can induce high titers of IgG antibodies (Abs) to a conjugated capsular polysaccharide (CPS), for example, that of the Meningococcus type C (MnC) (Lindberg et al., 1999). New conjugated vaccines to MnC using Tetanus toxoid (TT) and Diphtheria toxoid as carriers are now available, and have been effective in inhibiting Meningococcus type C meningitis in populations at risk (Miller et al., 2001; Rappuoli, 2001; Trotter et al., 2004; Richmond et al., 2001).

Both MnB and MnC are homopolymers of sialic acid with a difference in their glycosidic linkage: α(2-8) sialic acid in MnB compared to α(2-9) sialic acid in MnC. This seemingly minor difference leads to a major difference in the immunogenicity of these antigens; MnB is a very poor immunogen while MnC is an immunogenic TI antigen. MnB has structural homology with a self-antigen, the polysialylated adhesion molecule NCAM (PSA-NCAM) that is expressed in mammalian fetal tissues (Devi et al., 1997). In addition, cross-reactivity between anti-MnB Abs and brain extracts has been reported (Finne et al., 1983). Apparently, the structural homology of MnB with mammalian tissues leads to its very poor immunogenicity (Lifely et al., 1987). Thus, there is currently no effective vaccine against Meningococcus type B based on the CPS. Vaccines to Meningococcus type B, based on the outer membrane vesicle protein have been used (Morley et al., 2001), and others are undergoing clinical trials (Robertson et al., 2001; Perkins et al., 1998; Haneberg et al., 1998). Nevertheless, a conjugated MnB vaccine would be useful for the induction of protection against all the bacterial serotypes that share this CPS.

Conjugated vaccines composed of MnB attached to TT or CRM197 have had limited success in inducing IgG Abs to MnB (Devi et al., 1997; Bartoloni et al., 1995). Abs were mostly raised after the third injection, but those Abs were short-lived (Devi et al., 1997). Another approach, in which a chemically modified N-propionylated polysialic acid was conjugated to Meningococcal B Porin, was able to elicit bactericidal Abs to the CPS moiety in mice and monkeys (Fusco et al., 1997). Native MnB was not effective in inhibiting the bactericidal effect.

Thirteen different serogroups of meningococci have been identified on the basis of the immunological specificity of their capsular polysaccharide. Of these thirteen serogroups, five cause the majority of meningococcal disease; these include serogroups A, B, C, W135, and Y.

Vaccines suitable for immunization against groups A, C, Y and W-135 are commercially available. For example, Menomune® A/C/Y/W-135, a freeze-dried preparation of the group-specific polysaccharide antigens from *N. meningitidis* group A, group C, group Y and group W-135, and Menactra®, a meningococcal polysaccharide (groups A, C, Y and W-135)-diphtheria toxoid conjugate vaccine, have been approved for sale in the United States.

Disclosures directed to specific vaccine formulations comprising epitopes derived from CPS of meningococcal strains other than MnB were described, for example, in U.S. Pat. No. 5,425,946, WO 2005/000345, WO 2005/004909, WO 02/058737, and WO 2004/103400.

While many disclosures are directed to group B *N. meningitidis* vaccines, no such vaccine is currently available commercially. For example, U.S. Pat. No. 5,597,572 discloses a vaccine for immunizing against infection caused by Group B *N. meningitidis* microorganism, which comprises a purified protein antigenic complex weighing from 65 to 95 kDa, vesicles, and capsular polysaccharide. This vaccine is extracted from the cell membranes of the live microorganisms using detergent and enzyme.

U.S. Pat. No. 6,080,589 discloses capsular polysaccharides containing multiple sialic acid residues, particularly the Group B polysaccharide of *N. meningitidis*, modified by chemical reaction to randomly introduce pendant reactive residues of heterobifunctional linker molecules to the polysaccharide backbone. The introduction of the linker molecules to the polysaccharide chain between the termini enables the polysaccharide to be linked to a carrier molecule, such as a protein, to enhance the immunogenicity of the polysaccharide.

U.S. Pat. No. 6,350,449 relates to chemically modified group B polysaccharides of *N. meningitidis*, vaccines in which the respective modified polysaccharides are conjugated to a protein carrier, as well as antibodies to these conjugate vaccines. More specifically, the '449 patent provides group B meningococcal unsaturated N-acyl derivative polysaccharides, conjugates thereof, pharmaceutical compositions comprising conjugate molecules of group B meningococcal unsaturated N-acyl derivative polysaccharide fragments covalently bound to proteins, and the use of these compositions as vaccines.

U.S. Pat. No. 6,642,354 is directed to bactericidal antibodies against *N. menigitidis* serogroup B, which either do not cross-react or minimally cross-react with host tissue polysialic acid, useful for identifying molecular mimetics of unique epitopes found on *N. meningitidis* serogroup B or *E. coli* K1. The '354 patent discloses examples of such peptide mimetics that may elicit serum antibody capable of activating complement-mediated bacteriolysis of the pathogen.

U.S. Pat. No. 6,656,472 discloses a method of forming a multivalent immunogenic molecule tag comprising: treating at least two different carbohydrate molecules to obtain carbohydrate fragments thereof, forming a lysine-branching peptide containing at least two different T-helper cell epitopes as a carrier molecule anchored to a polymeric anchor wherein at least two carrier peptide segments have different terminal protecting groups, selectively removing one of the protecting groups, coupling a first one of the oligosaccharide fragments to the unprotected carrier peptide segment, selectively removing another of the protecting groups, coupling a second one of the oligosaccharide fragments to the unprotected carrier peptide segment, and cleaving the resulting molecule from the polymeric anchor. The oligosaccharide fragments may be derived, inter alia, from *N. meningitidis*, and are sized from about 2 to about 5 kDa.

U.S. Pat. No. 6,936,261 is directed to methods and vaccines for the prevention of diseases caused by *N. meningitidis* bacteria, particularly serogroup B strains, comprising the steps of: administering to a mammal a first preparation of microvesicles (MVs) from a first *N. meningitidis* species that is a member of a first serotype and of a first serosubtype, in an amount sufficient to elicit an immune response to epitopes present in said first preparation; and administering to said mammal a second preparation of MVs from a second *N. meningitidis* species that is a member of a second serotype and of a second serosubtype, in an amount sufficient to elicit an immune response to epitopes present in said second preparation; wherein the serotype or serosubtype of each of the first, second, and third *N. meningitidis* species is different, and wherein administering of the first, second, and third preparations is sufficient to elicit an immune response in said mammal, wherein said immune response confers protective immunity against a disease caused by more than one strain of *N. meningitidis* species.

Polysaccharide Vaccines for Cancer

PSA-NCAM is expressed in different tumors (Qu et al., 1996; Fukuda, 1996; Komminoth et al., 1994), and was suggested to be involved as an adhesion molecule in tumor metastasis (Friedl et al., 2004). Several patent applications are directed to utilizing PSA for cancer therapy.

For example, WO 01/47552 relates to an immunogenic composition comprising an α-(2-8)-polysialic acid-carrier conjugate and a saponin, wherein the α-(2-8)-polysialic acid-carrier conjugate comprises one or more α-(2-8)-polysialic acid polymers covalently linked to an immunogenic carrier, and wherein the median number of sialic acid units in each of the polymers is at least about 10. Preferred immunogenic carriers include keyhole limpet hemocyanin (KLH) and bovine serum albumin (BSA).

WO 01/09298 is directed to modifying the sialic acid component of a sialic acid unit-containing cell surface marker characteristic of cancerous mammalian cells, such as alpha 2-8 polysialic acid, so that cells normally expressing such a marker express instead a modified sialic acid unit-containing cell surface marker, which is strongly immunogenic. The modification is suitably N-acylation of a precursor of the sialic acid, so that the N-acylated precursor becomes chemically incorporated in the polysialic acid during its intracellular biochemical synthesis. The '298 application is further directed to vaccines comprising said conjugates or antibodies raised against said conjugates, useful for managing cancer conditions which involve cancer cells characterized by expression of modified sialic acid unit containing marker.

Krug et al. (2004) discloses a clinical study aimed to elicit an immune response against polysialic acid to target clinically inapparent residual disease in patients with SCLC who had successfully completed initial therapy. Krug et al. reports that vaccination with N-propionylated-polysialic acid-KLH, but not unmodified polysialic acid-KLH, resulted in a consistent high titer antibody response.

Pneumococcal Vaccines

Vaccines against encapsulated bacteria such as *S. pneumoniae* have included the CPS coat, since the CPS acts as the major Pn virulence factor (AlonsoDeVelasco et al., 1995). However, the Pn CPS is, like other polysaccharides, poorly immunogenic, especially in young children, the elderly and immunosuppressed adults. Conjugate vaccines have been designed using various protein carriers like TT as a source for T-cell epitopes conjugated to the CPS with the aim of supplying the help needed for IgG switching and immune memory (Goldblatt et al., 2000; Lesinski et al., 2001). However, the conjugation of a CPS to a protein carrier is usually insufficient to evoke a strong immune response, and an added adjuvant is often needed.

U.S. Pat. No. 6,855,321 is directed to polyepitope carrier proteins that comprise at least five $CD4^+$ T cell epitopes, for conjugation to capsular polysaccharides, including, inter alia, pneumococcal CPS.

U.S. Pat. No. 5,773,007 is directed to vaccine compositions comprising a long chain alkyl compound as an immunoadjuvant in combination with a bacterial polysaccharide protein conjugate.

U.S. Pat. No. 5,565,204 is directed to an immunogenic polysaccharide-protein conjugate obtained by reductive amination comprising (a) an oxidized polysaccharide derived from the capsular polysaccharide of *S. pneumoniae*, and (b) the pneumolysin protein of *S. pneumoniae* which is expressed recombinantly, where said pneumolysin is not toxoided or is not produced by site-specific mutagenesis prior to conjugation with said oxidized polysaccharide.

U.S. Pat. No. 7,018,637 discloses multivalent immunogenic molecules comprising a carrier molecule containing at least one functional T-cell epitope and multiple different carbohydrate fragments each linked to the carrier molecule and each containing at least one functional B-cell epitope. The carbohydrate fragments may be derived from pneumococcal or meningococcal CPS, among others.

Commercially available vaccines include e.g. Prevnar® and Pneumovax®. Prevnar® is a sterile solution of saccharides of the capsular antigens of *S. pneumoniae* serotypes 4, 6B, 9V, 14, 18C, 19F, and 23F individually conjugated to diphtheria CRM 197 protein. Pneumovax® 23 (Pneumococcal Vaccine Polyvalent) is a sterile, liquid vaccine for intramuscular or subcutaneous injection. It consists of a mixture of highly purified capsular polysaccharides from the 23 most prevalent or invasive pneumococcal types of *S. pneumoniae*, including the six serotypes that most frequently cause invasive drug-resistant pneumococcal infections among children and adults in the United States.

There remains an unmet medical need for providing additional effective vaccines conferring immunity against disease and infection. Improved vaccine compositions comprising conjugates of peptide carriers and antigen determinants, said conjugates having enhanced immunogenicity, would thus be highly beneficial.

SUMMARY OF THE INVENTION

The present invention is directed to the field of vaccination, particularly to novel compositions and methods comprising multimeric heat shock protein 60 (HSP60)-derived peptide carriers. It is now disclosed in accordance with the present invention that the known synthetic peptide carrier, p458, a Major Histocompatibility Complex (MHC) class II-restricted peptide derived from HSP60 (aa 458-474, also designated previously as p278m), or an analog or derivative thereof, provides significantly improved immunogenicity when administered as a multimeric conjugate comprising multiple copies of the p458 peptide carrier.

The invention is based, in part, on the surprising discovery, that p458 conjugated to bacterial capsular polysaccharides such as pneumococcal capsular polysaccharide type 4 (PS4) manifests innate adjuvant effects. Unexpectedly, the invention discloses that p458-PS4 conjugates having an increased peptide/polysaccharide ratio (w/w) that is greater than 1:1 stimulate mouse macrophages to secrete IL-12 and induce prolonged expression of PS4 on the macrophage surface, while other PS4 conjugates or PS4 or peptide alone fail to do so. Macrophages incubated with these conjugates induce long-term resistance to lethal Pn challenge when injected to mice.

Previous studies using p458-PS4 conjugates having a peptide/polysaccharide ratio (w/w) of between 0.9:1 to 0.5:1 failed to demonstrate that p458 activates macrophages directly (Konen-Waisman et al., 1998). The instant invention discloses that it is possible to improve the adjuvant effect of a p458 carrier-antigen conjugate by increasing the number of the p458 carrier peptides included in the conjugate.

Thus, the invention provides novel conjugates comprising multimeric p458 peptide carriers, vaccine compositions comprising them and methods of using same for inducing an enhanced immune response. Cell vaccines comprising antigen presenting cells (APC) that were exposed to the conjugates of the invention are further encompassed within the scope of the invention.

The present invention is also based, in part, on the surprising discovery, that low doses of conjugates of p458 and the poorly immunogenic Meningococcus type B capsular polysaccharide (MnB) are more effective than are conjugates of p458 and the more immunogenic Meningococcus type C capsular polysaccharide (MnC). It is now disclosed for the first time, that vaccine compositions comprising a MnB conjugate dose which is about ten times lower than the effective MnC conjugate dose used for vaccination may be effective for conferring immunity against meningitis and cancer. The present invention further demonstrates the efficacy of combined vaccines comprising both MnB and MnC conjugates.

Thus, additional embodiments of the present invention are directed to vaccine compositions and methods of using same, which are particularly useful for vaccination against meningitis and against tumors. These vaccine compositions comprise *Neisseria meningitidis* capsular polysaccharides, including Meningococcus type B and Meningococcus type C capsular polysaccharides, and a synthetic peptide carrier comprising a T cell epitope of HSP60. According to some embodiments, the synthetic peptide carrier is the known peptide p458, or an analog or derivative thereof. In other embodiments, the synthetic peptide carrier is Ec27, a peptide derived from *E. coli* HSP60 (GroEL, aa 391-410). According to further aspects of the present invention, dosage and administration regimes suitable for vaccination in humans are provided.

According to a first aspect of the present invention, there is provided a conjugate comprising an antigen covalently attached to HSP60-derived peptide sequences selected from the group consisting of:

(a) NEDQKIGIEIIKRTLKI,   (p458h; SEQ ID NO: 1)

(b) NEDQKIGIEIIKRALKI,   (p458; SEQ ID NO: 2)

(c) EGDEATGANIVKVALEA,   (p458mt; SEQ ID NO: 3)

(d) NEDQNVGIKVALRAMEA,   (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises a weight ratio of HSP60-derived peptide to antigen in excess of 1:1 (w/w);

with the proviso that said antigen is other than the capsular polysaccharide (CPS) Vi of *Salmonella typhi*.

In another aspect, the invention provides a conjugate comprising an antigen covalently attached to a multimeric carrier, in which the carrier comprises a plurality of peptide units comprising HSP60-derived sequences selected from the group of peptides consisting of:

(a) NEDQKIGIEIIKRTLKI,   (p458h; SEQ ID NO: 1)

(b) NEDQKIGIEIIKRALKI,   (p458; SEQ ID NO: 2)

(c) EGDEATGANIVKVALEA,   (p458mt; SEQ ID NO: 3)

(d) NEDQNVGIKVALRAMEA,   (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises at least about 30 peptide units per antigen molecule;

with the proviso that said antigen is other than the capsular polysaccharide (CPS) Vi of *Salmonella typhi*.

A multimeric carrier of the invention comprises a plurality of peptide units, in which each peptide may be conjugated directly to the antigen, or may be conjugated to the antigen indirectly via conjugation to other peptide units, forming e.g. a dendrimer or a fusion peptide comprising multiple peptide units in tandem.

Preferably, the conjugate comprises at least about 40, more preferably at least about 50, 80, or 100 peptide carrier units per antigen molecule. According to currently preferred embodiments, the conjugates of the invention comprise between about 50 and about 200 peptide carrier units per antigen molecule. In alternate embodiments, the conjugates of the invention comprise about 200 units or more per antigen molecule.

In another embodiment, the conjugate comprises at least one analog of p458h (SEQ ID NO: 1): $^{458}$NEDQKIGIEI-IKRTLKI$^{474}$ in which the residue $E^{459}$ is either E or D; the residue $D^{460}$ is either D or E; the residue $K^{462}$ is either K or R or ornithine (Orn); the residue $I^{463}$ is either I or L, V, M, F, norleucine (Nle) or norvaline (Nva); the residue $I^{465}$ residue is either I or L, V, M, F, Nle or Nva; the residue $E^{466}$ is either E or D; the residue $I^{467}$ is either I or L, V, M, F, Nle or Nva; the residue $I^{468}$ is either I or L, V, M, F, Nle or Nva; the residue $K^{469}$ is either K or R or Orn; the residue $R^{470}$ is either R, K or Orn; the residue $L^{472}$ in either L or I, V, M, F, Nle or Nva; the residue $K^{473}$ is either K or R or Orn; and the residue $I^{474}$ is either I or L, V, M, F, Nle or Nva.

In various embodiments, the antigen may include, but is not limited to, polypeptides, peptides, peptide derivatives, saccharides, glycolipids, lipoproteins and antibodies.

Antigens of particular interest are viral, fungal, parasite or bacterial antigens, or antigens associated with pathology, such as tumor-associated antigens. According to specific embodiments, the antigen may include protein, peptide or saccharide antigens derived from pathogens such as *Streptococcus pneumoniae* (for instance serotypes 1, 2, 3, 4, 5, 6B, 7F, 8, 9N, 9V, 10A, 11A, 12F, 14, 15B, 17F, 18C, 19F, 19A, 20, 22F, 23F, and 33F), *Neisseria* meningitidis (for example group A, B, C, W-135 and Y antigens, and peptide antigens such as Meningococcus B common epitope), *Staphylococcus aureus* (for instance CPS serotypes 5 and 8 and methicillin-resistant *Staphylococcus aureus* (MRSA) antigens), *Shigella flexneri* (For example serotypes 1a, 1b, 2a, 2b, 3a, 4a, 4b, 5b, X, Y, 6, 4bR), *Klebsiella pneumoniae* antigens (for instance serotype O1, O2a, O2a,c, O3, O4, O5 and O12 polysaccharide antigens) and enterotoxigenic *Escherichia coli*.

In a particular embodiment of the invention, said antigen is a bacterial CPS or a fragment thereof.

Advantageously, a conjugate of a bacterial CPS of about 50-100 kDa and a peptide carrier of the invention has a peptide/polysaccharide ratio (w/w) of at least 1:1, preferably at least 1.3:1, more preferably at least 1.5:1, 2:1, 4:1 or 8:1. According to a currently preferred embodiment, said conjugate has a peptide/polysaccharide ratio (w/w) of between 1.5:1 and 6:1.

In a particular embodiment, the antigen is a *Streptococcus pneumoniae* (*S. pneumoniae*) CPS. In further particular embodiments, the CPS includes, but is not limited to, CPS derived from *S. pneumoniae* serotypes 1, 2, 3, 4, 5, 6B, 7F, 8, 9N, 9V, 10A, 11A, 12F, 14, 15B, 17F, 18C, 19F, 19A, 20, 22F, 23F, and 33F, as detailed in Table 1 hereinbelow. In another particular embodiment, the *S. pneumoniae* CPS is a *S. pneumoniae* CPS type 4 (PS4).

In another particular embodiment, the antigen is a *Neisseria meningitidis* (*N. meningitidis*) CPS. In further particular embodiments, the *N. meningitidis* CPS includes, but is not limited to, CPS derived from *N. meningitidis* Group A, B, C, W-135 and Y. In another particular embodiment, said *N. meningitidis* CPS is a *N. meningitidis* group B CPS (MnB). In another particular embodiment, said *N. meningitidis* CPS is a *N. meningitidis* group C CPS (MnC).

In another aspect, the invention provides a conjugate comprising an antigen covalently attached to a multimeric carrier, in which the carrier comprises a plurality of peptide units comprising HSP60-derived sequences selected from the group of peptides consisting of:

(a) NEDQKIGIEIIKRTLKI, (p458h; SEQ ID NO: 1)

(b) NEDQKIGIEIIKRALKI, (p458; SEQ ID NO: 2)

(c) EGDEATGANIVKVALEA, (p458mt; SEQ ID NO: 3)

(d) NEDQNVGIKVALRAMEA, (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the antigen is a bacterial capsular polysaccharide (CPS) other than the CPS Vi of *Salmonella typhi*; and wherein said conjugate has a peptide/polysaccharide ratio (w/w) of at least 1:1, preferably at least 1.3:1, more preferably at least 1.5:1 and most preferably at least 2:1, or 4:1. According to a currently preferred embodiment, said conjugate has a peptide/polysaccharide ratio (w/w) of between 1.5:1 and 6:1.

In a particular embodiment, the antigen is a *S. pneumoniae* CPS. In further particular embodiments, the CPS includes, but is not limited to, CPS derived from *S. pneumoniae* serotypes 1, 2, 3, 4, 5, 6B, 7F, 8, 9N, 9V, 10A, 11A, 12F, 14, 15B, 17F, 18C, 19F, 19A, 20, 22F, 23F, and 33F, as detailed in Table 1 hereinbelow. In another particular embodiment, the *S. pneumoniae* CPS is a *S. pneumonia* CPS type 4 (PS4).

In another particular embodiment, the antigen is a *N. meningitidis* CPS. In further particular embodiments, the *N. meningitidis* CPS includes, but is not limited to, CPS derived from *N. meningitidis* Group A, B, C, W-135 and Y. In another particular embodiment, said *N. meningitides* CPS is a *N. meningitidis* group B CPS (MnB). In another particular embodiment, said *N. meningitidis* CPS is a *N. meningitidis* group C CPS (MnC).

In another aspect, there is provided a vaccine composition comprising at least one conjugate of the invention and a pharmaceutically acceptable carrier, excipient or diluent.

As demonstrated herein, the conjugates of the invention induce an effective immune response without an additional adjuvant. Thus, in another embodiment, the vaccines of the invention are formulated and administered without an additional adjuvant. Alternately and optionally, the vaccines may further comprise an additional adjuvant.

In a particular embodiment, the composition comprises a conjugate comprising a capsular polysaccharide of *Neisseria meningitidis* group B (MnB) covalently attached to a multimeric carrier in which the carrier comprises a plurality of peptide units comprising HSP60-derived sequences selected from the group of peptides consisting of:

(a) NEDQKIGIEIIKRTLKI, (p458h; SEQ ID NO: 1)

(b) NEDQKIGIEIIKRALKI, (p458; SEQ ID NO: 2)

(c) EGDEATGANIVKVALEA, (p458mt; SEQ ID NO: 3)

(d) NEDQNVGIKVALRAMEA, (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo;

and a pharmaceutically acceptable carrier, adjuvant, excipient or diluent, wherein the vaccine compositions comprise between about 0.1 and about 1000 µg of the conjugate, preferably between about 0.1 and about 100 µg of said conjugate, and more preferably between about 0.2 and about 25 µg of said conjugate.

In certain currently preferred embodiments, said conjugate comprises between about 30 and about 200 peptide units, preferably between about 40 and about 100 peptide units per antigen molecule.

In another embodiment, the vaccine composition further comprises a second conjugate, the second conjugate comprising a capsular polysaccharide of *Neisseria meningitidis* group C (MniC) covalently attached to a multimeric carrier in which the carrier comprises a plurality of peptide units comprising HSP60-derived sequences selected from the group of peptides consisting of:

(a) NEDQKIGIEIIKRTLKI, (p458h; SEQ ID NO: 1)

(b) NEDQKIGIEIIKRALKI, (p458; SEQ ID NO: 2)

(c) EGDEATGANIVKVALEA, (p458mt; SEQ ID NO: 3)

(d) NEDQNVGIKVALRAMEA, (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo.

In certain currently preferred embodiments, said conjugate comprises between about 30 and about 200 peptide units, preferably between about 40 and about 100 peptide units per antigen molecule.

In other embodiments, a suitable dose range for the MnC conjugates of the invention is between about 10 and about 1000 µg of the conjugate, preferably between about 20 and about 500 µg of the conjugate, and more preferably between about 40 and about 250 µg of the conjugate.

In certain other preferable embodiments, the MnB-specific vaccine compositions of the invention do not comprise an additional adjuvant.

In another aspect, the invention provides a vaccine composition comprising at least one multimeric carrier in admixture with at least one antigen, and a pharmaceutically acceptable carrier, excipient or diluent, wherein:

the multimeric carrier comprises a plurality of covalently attached peptide units comprising HSP60-derived sequences, in which each peptide unit is selected from the group of peptides consisting of:

(a) NEDQKIGIEIIKRTLKI,  (p458h; SEQ ID NO: 1)

(b) NEDQKIGIEIIKRALKI,  (p458; SEQ ID NO: 2)

(c) EGDEATGANIVKVALEA,  (p458mt; SEQ ID NO: 3)

(d) NEDQNVGIKVALRAMEA,  (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the multimeric carrier comprises at least about 30 covalently attached peptide units.

In another embodiment, the multimeric carrier comprises at least about 40, preferably at least about 50, and more preferably at least about 80, 100, or, in other embodiments, at least about 200 covalently attached peptide units.

In various embodiments, the antigen may include, but is not limited to, polypeptides, peptides, peptide derivatives, saccharides, glycolipids, lipoproteins and antibodies.

For example, without limitation, the antigen may include protein, peptide or saccharide antigens derived from pathogens such as *Streptococcus pneumoniae, Neisseria meningitidis, Staphylococcus aureus, Shigella flexneri, Klebsiella pneumoniae* and enterotoxigenic *Escherichia coli.*

In a particular embodiment of the invention, said antigen is a bacterial CPS or a fragment thereof.

In a particular embodiment, the antigen is a *S. pneumoniae* CPS. In further particular embodiments, the CPS includes, but is not limited to, CPS derived from *S. pneumoniae* serotypes 1, 2, 3, 4, 5, 6B, 7F, 8, 9N, 9V, 10A, 11A, 12F, 14, 15B, 17F, 18C, 19F, 19A, 20, 22F, 23F, and 33F, as detailed in Table 1 hereinbelow. In another particular embodiment, the *S. pneumoniae* CPS is a *S. pneumoniae* CPS type 4 (PS4).

In another particular embodiment, the antigen is a *N. meningitidis* CPS. In further particular embodiments, the *N. meningitidis* CPS includes, but is not limited to, CPS derived from *N. meningitidis* Group A, B, C, W-135 and Y. In another particular embodiment, said *N. meningitidis* CPS is a *N. meningitidis* group B CPS (MnB). In another particular embodiment, said *N. meningitidis* CPS is a *N. meningitidis* group C CPS (MnC).

Another aspect of the present invention is directed to a vaccine composition comprising a capsular polysaccharide and a peptide derived from *E. coli* HSP60 (GroEL), the peptide being selected from the group consisting of: KKARVEDALHATRAAVEEGV (SEQ ID NO:5; Ec27), KKDRVTDALNATRAAVEEGI (SEQ ID NO:6; Ec27h), and analogs, fragments, derivatives, conjugates and salts thereof, wherein the CPS is selected from *N. meningitidis* CPS and *S. pneumoniae* CPS.

In certain particular embodiments, the CPS is selected from the group consisting of MnB, MnC and mixtures thereof. In another particular embodiment, the CPS is MnB. In another particular embodiment, the CPS is PS4.

In certain other embodiments, the CPS may be conjugated to said peptide. In alternate embodiments, the composition may comprise an admixture of said CPS and said peptide.

Preferably, the composition comprises a plurality of covalently attached peptides having an amino acid sequence as set forth in any one of SEQ ID NOS:5 and 6 and analogs, fragments, derivatives, conjugates and salts thereof.

In other embodiments, the CPS is further conjugated to a second carrier. In certain other particular embodiments, the second carrier comprises HSP60-derived sequences selected from the group of peptides consisting of:

(a) NEDQKIGIEIIKRTLKI,  (p458h; SEQ ID NO: 1)

(b) NEDQKIGIEIIKRALKI,  (p458; SEQ ID NO: 2)

(c) EGDEATGANIVKVALEA,  (p458mt; SEQ ID NO: 3)

(d) NEDQNVGIKVALRAMEA,  (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo.

In another embodiment, said carrier is a multimeric carrier comprising at least about 30 covalently attached copies of the HSP60-derived sequences.

In another aspect, there is provided a method for enhancing the immunogenicity of an antigen comprising conjugating the antigen to a plurality of peptide units comprising HSP60-derived sequences, in which each peptide unit is selected from the group of peptides consisting of:

(a) NEDQKIGIEIIKRTLKI,  (p458h; SEQ ID NO: 1)

(b) NEDQKIGIEIIKRALKI,  (p458; SEQ ID NO: 2)

(c) EGDEATGANIVKVALEA,  (p458mt; SEQ ID NO: 3)

(d) NEDQNVGIKVALRAMEA,  (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the antigen is conjugated to at least about 30 peptide units;

with the proviso that said antigen is other than the capsular polysaccharide (CPS) Vi of *Salmonella typhi*.

In another aspect, there is provided a method for immunizing a subject in need thereof, comprising administering to the subject an effective amount of a vaccine composition of the invention.

In another aspect, the invention provides a method for immunizing a subject in need thereof against *Neisseria meningitidis* infection, comprising the step of administering to the subject a prophylactically effective amount of a vaccine composition comprising at least one conjugate, the conjugate comprising a capsular polysaccharide of *Neisseria meningitidis* group B (MnB) covalently attached to a multimeric carrier, in which the carrier comprises a plurality of peptide units comprising HSP60-derived sequences selected from the group of peptides consisting of:

(a) NEDQKIGIEIIKRTLKI,    (p458h; SEQ ID NO: 1)

(b) NEDQKIGIEIIKRALKI,    (p458; SEQ ID NO: 2)

(c) EGDEATGANIVKVALEA,    (p458mt; SEQ ID NO: 3)

(d) NEDQNVGIKVALRAMEA,    (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo;

and a pharmaceutically acceptable carrier, adjuvant, excipient or diluent, wherein the vaccine compositions comprise between about 0.1 and about 1000 µg of the conjugate, preferably between about 0.1 and about 100 µg of said conjugate, and more preferably between about 0.2 and about 25 µg of said conjugate.

In another aspect, the invention provides a method of treating cancer in a subject in need thereof, comprising the step of administering to the subject a therapeutically effective amount of a vaccine composition comprising at least one conjugate, the conjugate comprising a capsular polysaccharide of *Neisseria meningitidis* group B (MB) covalently attached to a multimeric carrier, in which the carrier comprises a plurality of peptide units comprising HSP60-derived sequences selected from the group of peptides consisting of:

(a) NEDQKIGIEIIKRTLKI,    (p458h; SEQ ID NO: 1)

(b) NEDQKIGIEIIKRALKI,    (p458; SEQ ID NO: 2)

(c) EGDEATGANIVKVALEA,    (p458mt; SEQ ID NO: 3)

(d) NEDQNVGIKVALRAMEA,    (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo;

and a pharmaceutically acceptable carrier, adjuvant, excipient or diluent, wherein the vaccine composition comprises between about 0.1 and about 1000 µg of the conjugate, preferably between about 0.1 and about 100 µg of said conjugate, and more preferably between about 0.2 and about 25 µg of said conjugate.

The MnB-specific compositions of the invention are suitable for the treatment of tumors expressing α(2-8) polysialic acid, including, but not limited to malignancies of neuroectodermal origin (e.g. small cell lung cancer), neuroblastoma, thyroid carcinoma, primary C-cell hyperplasia, rhabdomyosarcoma, natural killer cell derived-lymphoma, and Wilm's tumor.

In another aspect, the invention provides a method of inhibiting tumor metastasis in a subject in need thereof, comprising the step of administering to the subject a therapeutically effective amount of a vaccine composition comprising at least one conjugate, the conjugate comprising a capsular polysaccharide of *Neisseria meningitides* group B (MnB) covalently attached to a multimeric carrier, in which the carrier comprises a plurality of peptide units comprising HSP60-derived sequences selected from the group of peptides consisting of:

(a) NEDQKIGIEIIKRTLKI,    (p458h; SEQ ID NO: 1)

(b) NEDQKIGIEIIKRALKI,    (p458; SEQ ID NO: 2)

(c) EGDEATGANIVKVALEA,    (p458mt; SEQ ID NO: 3)

(d) NEDQNVGIKVALRAMEA,    (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo;

and a pharmaceutically acceptable carrier, adjuvant, excipient or diluent, wherein the vaccine compositions comprise between about 0.1 and about 1000 µg of the conjugate, preferably between about 0.1 and about 100 µg of said conjugate, and more preferably between about 0.2 and about 25 µg of said conjugate.

Other embodiments of the invention are directed to antigen-loaded (pulsed) antigen presenting cells (APC) obtained by incubating a population of APC with a multimeric conjugate of the invention, useful for the preparation of cell vaccines. Thus, there is provided, in another aspect, a cell vaccine composition comprising APC exposed in culture, under conditions promoting uptake and processing of an antigen, to a conjugate comprising an antigen covalently attached to a multimeric carrier, in which the carrier comprises a plurality of peptide units comprising HSP60-derived sequences selected from the group of peptides consisting of:

(a) NEDQKIGIEIIKRTLKI,    (p458h; SEQ ID NO: 1)

(b) NEDQKIGIEIIKRALKI,    (p458; SEQ ID NO: 2)

(c) EGDEATGANIVKVALEA,    (p458mt; SEQ ID NO: 3)

(d) NEDQNVGIKVALRAMEA,    (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises at least about 30 peptide units per antigen molecule, to provide antigen-expressing APC.

In various embodiments, the APC are selected from macrophages, B-cells and dendritic cells.

In another aspect, the invention provides a method of stimulating an immune response in a subject in need thereof, comprising the steps of:

(i) obtaining antigen presenting cells (APC) from the subject, or from a donor histocompatible with said subject;

(ii) exposing the APC in culture, under conditions promoting uptake and processing of an antigen, to an immunogenic conjugate, to provide antigen-expressing APC; and (iii) administering an effective amount of the antigen-expressing APC to said subject;

wherein the immunogenic conjugate comprises an antigen covalently attached to a multimeric carrier, in which the carrier comprises a plurality of peptide units comprising HSP60-derived sequences selected from the group of peptides consisting of:

(a) NEDQKIGIEIIKRTLKI,   (p458h; SEQ ID NO: 1)

(b) NEDQKIGIEIIKRALKI,   (p458; SEQ ID NO: 2)

(c) EGDEATGANIVKVALEA,   (p458mt; SEQ ID NO: 3)

(d) NEDQNVGIKVALRAMEA,   (p458e; SEQ ID NO: 4)

Figure 11:
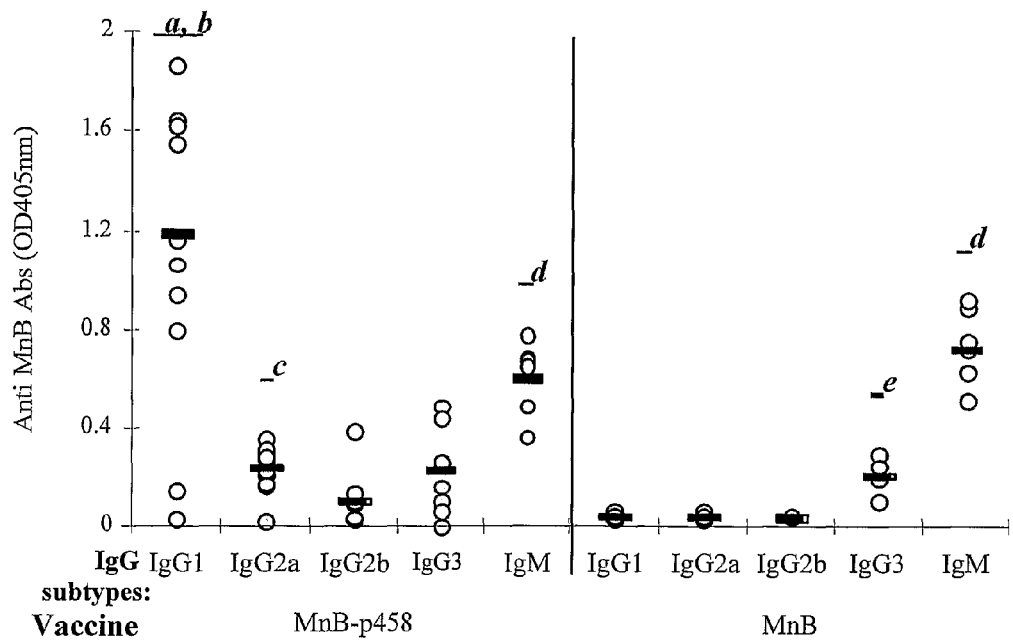

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises at least about 30 peptide units per antigen molecule.

In various embodiments, the APC are selected from macrophages, B-cells and dendritic cells.

Other objects, features and advantages of the present invention will become clear from the following description and drawings.

BRIEF DESCRIPTION OF THE DRAWINGS

FIG. 1. PS4-p458 but not PS4-p30 induces protection when administered in PBS. Ten BALB/c mice per group were immunized once s.c. with 2 μg per mouse of PS4-p458, PS4-p30 or with PS4 alone in IFA (A) or in PBS (B). One month later, the mice were challenged with 10000 Pn CFU* (A) or with 100 Pn CFU (B). * 1 CFU=$LD_{50}$ times 1.

FIG. 2. PS4-p458 induces the RAW macrophage cell line to secrete IL-12. RAW cells were incubated for 24 hours with 20 μg/ml of PS4-p458, PS4-p30, p458, p30, PS4, LPS (100 ng/ml), or with serum-free medium alone (None). In parallel, RAW cells were also pre-treated with Polymixin B (PmB) (10 μg/ml) for 30 minutes, and then incubated with the indicated treatments. Supernatants were collected and tested by ELISA for the presence of IL-12. Only PS4-p458 or LPS induced IL-12; PmB inhibited the effect of LPS, but not that of PS4-p458.

FIG. 3. RAW cells pulsed with PS4-p458, but not with PS4-p30 or PS4, show late expression of PS4 on the surface. RAW cells were pulsed with 100 μg/ml PS4-p458, PS4-p30 or PS4 alone for 5, 15 or 30 minutes. Then the cells were fixed, and the presence of PS4 at the cell surface was detected by anti-PS4 antibodies and FITC-conjugated anti-antibodies and followed by fluorescence microscopy ("None" means no Abs). Only the cells that had been pulsed with PS4-p458 manifested PS4 at the surface at 30 minutes.

FIG. 4. PS4-p458 induces the prolonged and late appearance of PS4 on the surface of macrophages with intact TLR-4. RAW cell-line macrophages (A), peritoneal macrophages obtained from C3HeB/Fej mice with wild-type TLR-4 (B) or from TLR-4-mutant C3H/Hej mice (C) were incubated for various times with 20 μg/ml of PS4-p458 or PS4. The cells were then fixed and stained for surface PS4 by anti-PS4 antibodies and FITC-conjugated anti-antibodies and followed by fluorescence microscopy. Fluorescence intensity was determined by FACS and expressed as the Fluorescence Index (FI): fluorescence intensity divided by the background of un-pulsed macrophages (Background). Peritoneal macrophages from the TLR-4-mutant C3H/Hej mice did not manifest the late, prolonged expression of surface PS4.

FIG. 5. RAW cells pulsed with PS4-p458 induce resistance to a lethal Pn challenge. RAW cells were pulsed with 20 μg/ml of PS4-p458, PS4-p30, PS4 alone or with medium alone (None) for 30 minutes. The cells were then washed with PBS, irradiated and injected i.p to 5 BALB/c mice per group. The mice were challenged three weeks later with 1000 Pn CFU.

FIG. 6. LPS stimulation induces late appearance of PS4 on the macrophage surface, inhibitable by Cytochalasin D (CytD). RAW cells were stimulated with 5 μg/ml LPS (+LPS) for 2 hours or not (−LPS). A third group of RAW cells were stimulated with LPS and then washed and incubated with 20 μM CytD for one hour (+LPS+CytD). Then the cells were washed and pulsed with 2.5 μg/ml FITC-labeled PS4 (mixed with 100 μg/ml unlabeled PS4) for 5, 30, 60 or 90 minutes. The cells were then fixed and stained with Cy5 for H-$2D^d$ (MHC-I). (A) Representative images; FITC (green), Cy5 (red). (B) A quantitative analysis of PS4-FITC intensity on the cell surface. The analysis was done using SimplePCI software. The graph represents the mean FITC intensity of five random pictures at each time point.

FIG. 7. Expression of labeled PS4 on the RAW cell surface is specifically inhibited by incubation with cold PS4. RAW cells were pre-incubated with various concentrations (0-750 μg/ml) of unlabeled PS4 or dextran for one hour, and then FITC-labeled PS4 (2.5 μg/ml) was added for an additional hour. The cells were then fixed and stained for H-$2D^d$. FITC (green), Cy5 (red). Unlabeled PS4 specifically inhibited the surface expression of labeled PS4.

FIG. 8. Mice immunized with macrophages expressing PS4 are long-term resistant to lethal Pn challenge, and have no Pn bacteria in the bloodstream after the challenge. Intact but not lysed PS4-pulsed RAW cells induce resistance. (A) RAW cells were either pre-stimulated or not with LPS (5 μg/ml, 2 hours), and then pulsed with PS4 for 0, 5, 30 or 60 minutes. The cells were then irradiated and injected i.p ($2\times10^6$) to 5-10 BALB/c mice per group. After three weeks, the mice were challenged i.p with 100 Pn CFU per mouse followed for survival. (B) After the challenge, blood samples were taken from each mouse 2, 8 and 18 hours and plated for CFU number determination. (C) RAW cells or a breast cancer cell line (4T1) were activated with LPS and pulsed with PS4, then irradiated (Irr.), GH-fixed (GH) or hypotonically lysed (Lysis), as indicated in the graph. The cells were then injected i.p to 5-10 BALB/c mice per group. After three weeks, the mice were challenged with 100 Pn CFU and followed for survival. Hypotonic cell lysis was done by incubating the cells in ice-cold DDW for 15 minutes and then passing the cells through a 27 g syringe needle several times. GH-fixation was done by incubating the cells with 1% of Gluteraldehyde for 20 minutes at room temperature. (D) Mice were challenged 30, 60 or 90 days after immunization.

FIG. 9. Vaccine doses. Groups of 6 mice were vaccinated 3 times at two weeks intervals with 0.2, 2 or 20 μg per mouse of MnB-p458, MnB+p458 (a), or with either 2 or 20 μg per mouse of MnC-p458 or MnC+p458 (b), and bled one month later. The sera of individual mice were assayed by ELISA for anti-MnB or anti-MnC IgG Abs.

FIG. 10. Three injections of the MnB-p458 vaccine are needed to induce anti-MnB IgG. Groups of 6 mice were vaccinated 3 times with 2 μg per mouse of MnB-p458, MnB+p458 or MnB and bled 2 weeks after the first, second and third vaccinations. The sera of individual mice were assayed by ELISA for IgG Ab to MnB.

FIG. 11. MnB-p458 induces anti-MnB IgG1 Ab. Mice were vaccinated 3 times with MnB-p458 (10 mice) or MnB (5 mice) and bled one month following the last immunization. The sera of individual mice were assayed by ELISA for the presence of anti-MnB IgG1 IgG2a IgG2b IgG3 or IgM Abs. Note that mice vaccinated with MnB-p458 and did not produce IgG1 Abs, lacked also other IgG subtypes.

Figure 12:
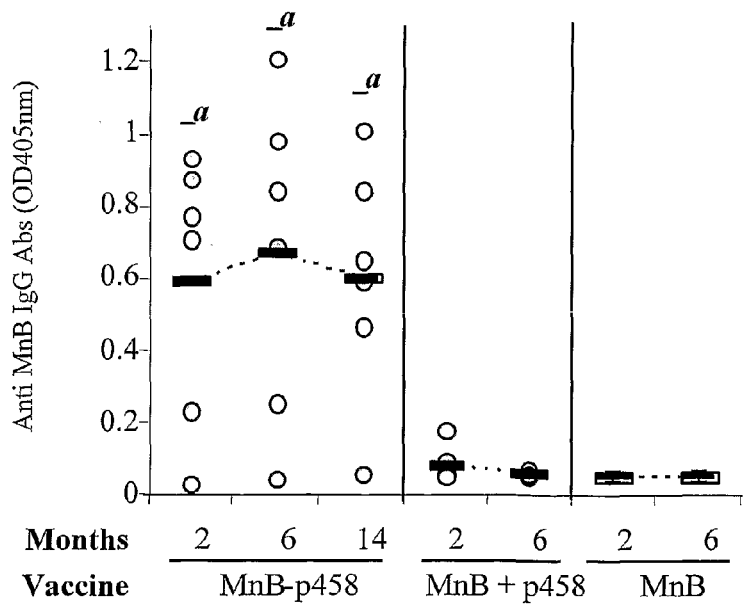

FIG. 12. Long lasting Abs to MnB. Groups of 6 mice were injected 3 times with MnB-p458, MnB+p458 or with MnB alone. The mice were bled at the age of 6 months (2 months after immunization), at the age of 10 months (6 months after immunization) and at the age of 18 months (14 months after immunization). The sera of individual mice were tested by ELISA for Ab to MnB.

Figure 13:
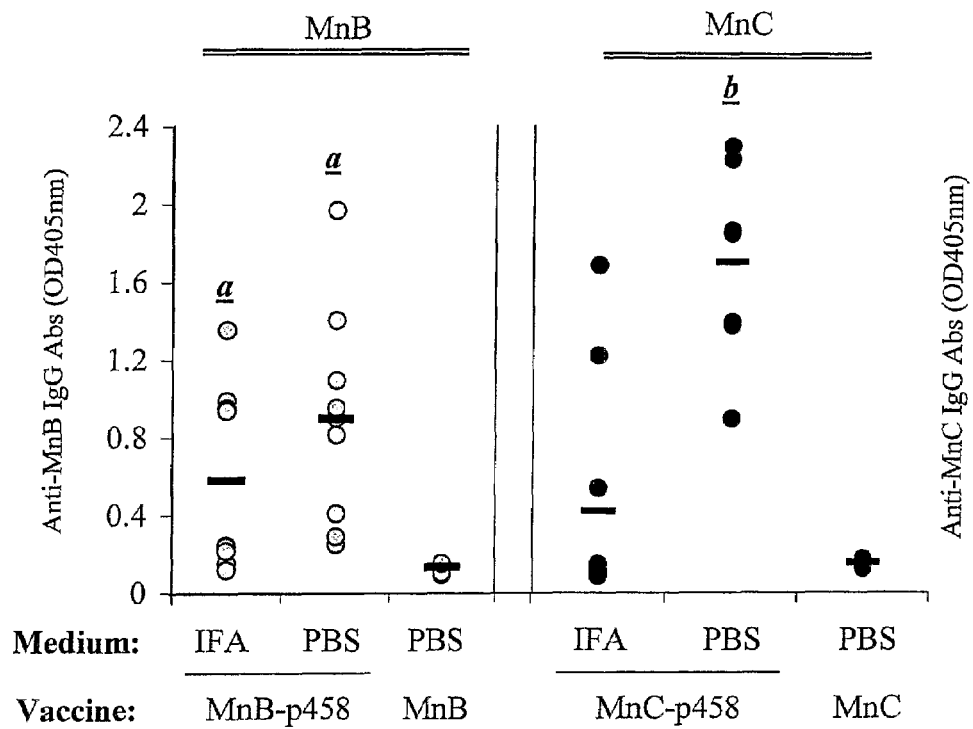

FIG. 13. PBS is an effective vehicle to induce anti-MnB and -MnC IgG Abs. Groups of 8-9 mice were immunized 3 times with 2 mg of MnB-p458 or MnC-p458 in IFA or in PBS, or with MnB or MnC in PBS. The mice were bled one month following the last immunization and the sera were tested individually by ELISA for anti-MnB Abs.

Figure 14:
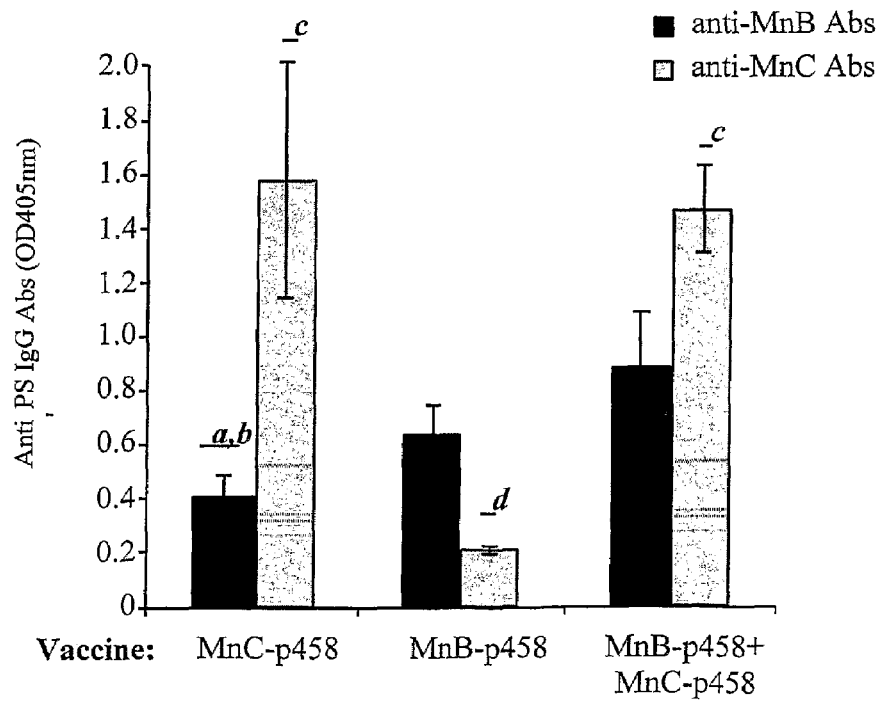

FIG. 14. Reciprocal induction of cross-reactive Abs to MnB or MnC. Mice were injected 3 times with MnB-p458, MnC-p458 or with MnB-p458+MnC-p458. The mice were bled 4 weeks after the last boost. The sera of individual mice were tested by ELISA for Ab to MnB or MnC. The mean and standard error were determined.

FIG. 15. Mice immunized with macrophages or dendritic cells expressing PS4 or PS3 are resistant to lethal challenge by Pn4 or Pn3, respectively. (A) RAW cells were stimulated or not with LPS and pulsed with PS4 or PS3. The cells were irradiated and injected i.p to female BALB/c mice. Three weeks later, the mice were challenged with Pn4 or Pn3 bacteria. (B) Bone marrow-derived dendritic cells (BMDC) were stimulated with LPS or not. Then, the cells were pulsed with PS4 or PS3 and injected i.p to female BALB/c mice. Part of the cells was injected following irradiation (labeled "LPS+PS irr."). Three weeks later, the mice were challenged with Pn4 or Pn3 bacteria.

DETAILED DESCRIPTION OF THE INVENTION

The present invention is directed to improved vaccine compositions having enhanced immunogenicity and to methods of using same. Specifically, the compositions and methods include immunogenic conjugates containing peptide carriers derived from heat shock protein 60 (HSP60). It is herein disclosed for the first time that the known synthetic peptide carrier, p458, and analogs and derivatives thereof, confers significantly improved immunogenicity when administered as a multimeric conjugate comprising a plurality of peptide carrier units conjugated to each antigen. The invention further provides administration doses and schedules that are particularly effective against meningococcal and pneumococcal infection and for cancer therapy. Novel cell vaccine compositions comprising antigen presenting cells loaded with multimeric p458 conjugates are also provided.

According to certain embodiments, the invention is directed to immunogenic conjugates comprising an antigen covalently attached to a multimeric p458 carrier, and to vaccine compositions comprising them. In other embodiments, the vaccine compositions comprise an admixture of the antigen and the multimeric p458 carrier.

A "multimeric p458 carrier" of the invention comprises a plurality of peptide carrier units comprising HSP60-derived sequences selected from the group of peptides consisting of:

(a) NEDQKIGIEIIKRTLKI, (p458h; SEQ ID NO: 1)
(b) NEDQKIGIEIIKRALKI, (p458; SEQ ID NO: 2)
(c) EGDEATGANIVKVALEA, (p458mt; SEQ ID NO: 3)
(d) NEDQNVGIKVALRAMEA, (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises at least about 30 peptide carrier units.

In another embodiment, antigens included in the immunogenic conjugates of the invention are other than the capsular polysaccharide (CPS) Vi of *Salmonella typhi*.

Preferably, the conjugate comprises at least about 40, more preferably at least about 50, 80, or 100 peptide carrier units per antigen (Ag) molecule. According to currently preferred embodiments, the conjugates of the invention comprise between about 50 and about 200 peptide carrier units per Ag molecule. In alternate embodiments, the conjugates of the invention comprise at least about 200 units per Ag molecule.

In another aspect, there is provided a conjugate comprising an antigen covalently attached to HSP60-derived peptide sequences selected from the group consisting of:

(a) NEDQKIGIEIIKRTLKI, (p458h; SEQ ID NO: 1)
(b) NEDQKIGIEIIKRALKI, (p458; SEQ ID NO: 2)
(c) EGDEATGANIVKVALEA, (p458mt; SEQ ID NO: 3)
(d) NEDQNVGIKVALRAMEA, (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises a weight ratio of HSP60-derived peptide to antigen in excess of 1:1 (w/w);

with the proviso that said antigen is other than the capsular polysaccharide (CPS) Vi of *Salmonella typhi*.

The invention further provides vaccine compositions comprising these conjugates and multimeric p458 carriers and methods of using same, as detailed herein.

Other embodiments of the invention are directed to immunogenic conjugates comprising capsular polysaccharides and an Ec27 peptide carrier and to vaccine compositions comprising them. In other embodiments, the vaccine compositions comprise an admixture of the antigen and the Ec27 peptide carrier. An "Ec27 peptide carrier" of the invention is a peptide derived from *E. coli* HSP60 (GroEL) selected from the group consisting of: KKARVEDALHATRAAVEEGV (SEQ ID NO:5; Ec27), KKDRVTDALNATRAAVEEGI (SEQ ID NO:6; Ec27h), and analogs, fragments, derivatives, conjugates and salts thereof. In another embodiment, the immunogenic conjugates comprising the Ec27 peptide carriers of the invention comprise an antigen selected from *N. meningitidis* CPS and *S. pneumoniae* CPS.

Preferably, these immunogenic conjugates and compositions comprise a plurality of covalently attached Ec27 peptide carriers. In other preferable embodiments, the CPS is further conjugated to, or formulated in combination with, a multimeric p458 carrier of the invention.

In other embodiments, the compositions comprising the multimeric p458 carriers of the invention further comprise an Ec27 peptide carrier of the invention.

Peptide Synthesis

The polypeptides and peptides of the invention may be synthesized using any recombinant or synthetic method known in the art, including, but not limited to, solid phase (e.g. Boc or f-Moc chemistry) and solution phase synthesis methods. For solid phase peptide synthesis, a summary of the many techniques may be found in: Stewart and Young, 1963; and Meienhofer, 1973. For a review of classical solution synthesis, see Schroder and Lupke, 1965. Non-limitative examples for peptide synthesis and purification are presented in the Examples section hereinbelow.

The active peptide carriers according to the invention are characterized as being highly charged, i.e. of strong electric properties (7 out of 17 constituent amino acid residues of p458 are either negatively or positively charged) and highly hydrophobic (6 amino acid residues). The peptide p458h is further characterized as possessing a polar negatively-charged N-terminal domain, a polar positively-charged C-terminal domain and a highly hydrophobic core. These overall features should be maintained in order to preserve efficacy. Thus, following the above general outline certain amino acids substitution will lead to active peptides. More specifically, positions 6, 8, 10, 11, 15 and 17 in the p458 peptide chain (corresponding to positions 463, 465, 467, 468, 472 and 474 of the human HSP60 molecule) can be occupied by either I or L or by other hydrophobic amino acids, natural, such as V, M, or F, or unnatural amino acids, such as norleucine (Nle) or norvaline (Nva). Positions 5, 12, 13 and 16 in the p458h chain (corresponding to positions 462, 469, 470 and 473 of the human HSP60 molecule) can be occupied by either K or R or by unnatural positively charged amino acids, such as ornithine (Orn). Interchange of E and D may also lead to active derivatives.

The term "analogs" relates to peptides obtained by replacement, deletion or addition of amino acid residues to the sequence, optionally including the use of a chemically derivatized residue in place of a non-derivatized residue, as long as they have the capability of enhancing substantially the immunogenicity of capsular polysaccharide molecules. Analogs, in the case of p458, are peptides such that at least 70%, preferably 90-100%, of the electric properties and of the hydrophobicity of the peptide molecule are conserved. These peptides can be obtained, without limitation, according to the instructions in the paragraph hereinbefore. Thus for example, an analog or derivative of p458h (SEQ ID NO: 1) has at least 70% amino similarity in its amino acid composition to human HSP60 from position 458 to position 474, as defined by the BLOSUM-80, 62 or 45 amino acid substitution matrices (Henikoff and Henikoff, 1992), said peptide, analog or derivative being capable of increasing substantially the immunogenicity of the antigen when the conjugate is administered in vivo.

By "substantially increasing" the immunogenicity of an Ag (e.g. a CPS) molecule it is meant to comprise both the induction of an increase in the level of Abs against said Ag as well as the presentation of said Abs as mainly of the IgG isotype. Alternatively, the term may represent an increase in antigen-specific T cell response, as measured, for example, as increased antigen-specific T cell proliferation or cytokine secretion, using methods well known in the art. Increase in the immunogenicity of the Ag may be also represented by innate cell parameters as measured, for example, as increased presentation and transportation of the antigen, and change in the cytokine profile (e.g., increased IL-12 secretion from macrophages in culture or increased IFNγ levels in the blood are indicative of increased immunogenicity). Certain non-limitative examples of determining Ab level and isotype and cytokine secretion are presented in the Examples below.

The amino acid residues described herein are preferred to be in the "L" isomeric form. However, residues in the "D" isomeric form can be substituted for any L-amino acid residue, as long as the peptide substantially retains the desired functional property. Use of "D" amino acids may be used as is known in the art to increase the stability or half life of the resultant peptide.

Whenever peptide carriers are mentioned in the invention, also salts and functional derivatives thereof are contemplated, as long as they are able to substantially enhance the immunogenicity of the Ag (e.g. bacterial polysaccharide). Thus, the present invention encompasses peptides containing non-natural amino acid derivatives or non-protein side chains.

The term peptide derivative includes any chemical derivative of the peptide carriers of the invention having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-allyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide carrier can differ from the natural sequence of the peptides of the invention by chemical modifications including, but are not limited to, terminal-$NH_2$ acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

Addition of amino acid residues may be performed at either terminus of the peptide carriers of the invention for the purpose of providing a "linker" by which the Ag (e.g. bacterial polysaccharides) can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

Antigens

In various embodiments, the antigen may include, but is not limited to, polypeptides, peptides, peptide derivatives, saccharides (e.g. polysaccharides and oligosaccharides), lipoproteins, glycolipids, and antibodies, including active fragments thereof.

Antigens of particular interest are viral, fungal, parasite or bacterial antigens, or antigens associated with pathology, such as tumor-associated antigens.

According to certain particular embodiments, antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')$_2$. Such active fragments are well known in the art and may be readily isolated or synthesized by a skilled artisan.

According to other specific embodiments, the antigen may include protein, peptide or saccharide antigens derived from bacteria such as *Streptococcus pneumoniae* (for instance serotypes 1, 2, 3, 4, 5, 6B, 7F, 8, 9N, 9V, 10A, 11A, 12F, 14, 15B, 17F, 18C, 19F, 19A, 20, 22F, 23F, and 33F), *Neisseria meningitidis* (for example group A, B, C, W-135 and Y antigens, and peptide antigens such as Meningococcus B common epitope; see, e.g., Pizza et al., 2000), *Staphylococcus aureus* (for instance CPS serotypes 5 and 8; see e.g. von Eiff et al., 2007; and methicillin-resistant *Staphylococcus aureus* (MRSA) antigens, see e.g. Burnie et al., 2000), *Shigella flexneri* (For example serotypes 1a, 1b, 2a, 2b, 3a, 4a, 4b, 5b, X, Y, 6, 4bR; see e.g. Carlin et al., 1987), *Klebsiella pneumoniae* antigens (for instance serotype O1, O2a, O2a,c, O3, O4, O5 and O12 polysaccharide antigens; see, e.g., Vinogradov et al., 2002) and enterotoxigenic *Escherichia coli* (see, e.g. Feng et al., 2007).

In a particular embodiment of the invention, said antigen is a bacterial CPS or a fragment thereof.

In a particular embodiment, the antigen is a *Streptococcus pneumoniae* (*S. pneumoniae*) antigen, e.g. a *S. pneumoniae* protein, peptide or CPS. In further particular embodiments, the CPS includes, but is not limited to, CPS from pathogenic serotypes of *S. pneumoniae* known in the art (see, e.g., Robbins et al., 1983). It should be noted, that there are two common classification designations systems: the U.S. and the Danish. U.S. and Danish designations of certain exemplary Pn serotypes are listed in Table 1 below:

CPS can be prepared by standard techniques known to those of skill in the art. In certain embodiments, CPS are purified from bacterial cultures. Various CPS are also commercially available and may be obtained e.g. from the American Type Culture Collection (ATCC, Manassas, Va.) or from manufacturers such as Sigma Chemicals Co. (St. Louis, Mo.). A non-limitative example for CPS preparation is presented in the Examples below. It will be appreciated that the isolation and purification procedures described in the Examples hereinbelow are not the only ones which may be utilized, and that other published procedures are available, for example those described by U.S. Pat. No. 6,350,449.

Capsular polysaccharides may be subjected to an activation step, whereby the polysaccharide is treated chemically to provide chemical groups capable of reacting with the carrier protein. A non-limitative example of activating CPS using cyanogen bromide and triethylamine is presented in the Examples below.

Other antigens such as proteins and peptides may be isolated from their natural source or obtained by chemical synthesis or recombinant methods known in the art (see e.g. Sambrook et al., 2001; see also Pizza et al., 2000; von Eiff et al., 2007; Burnie et al., 2000; Carlin et al., 1987; Vinogradov et al., 2002; and Feng et al., 2007 for antigen synthesis/isolation methods).

Conjugation Methods

A multimeric carrier of the invention comprises a plurality of peptide carrier units, in which each peptide carrier may be conjugated directly to the antigen, or may be conjugated to the antigen indirectly via conjugation to other peptide carriers, forming e.g. a dendrimer or a fusion peptide comprising multiple peptide carrier units in tandem.

A conjugate comprising a bacterial CPS and multiple copies of the peptide carrier may be created, for example, by means of chemically conjugating the CPS with the carrier peptides, directly or via a spacer, using methods well known in the art. Both homobifunctional and heterobifunctional linkers are available commercially, for example, from Pierce Chemical Company, Rockford, Ill., USA.

TABLE 1 designations of Pn serotypes

| | Pneumococcal Type | | | | | | | | | | | | | | | | | | | | | |
|---|---|---|---|---|---|---|---|---|---|---|---|---|---|---|---|---|---|---|---|---|---|---|
| U.S. designation | 1 | 2 | 3 | 4 | 5 | 8 | 9 | 12 | 14 | 17 | 19 | 20 | 22 | 23 | 25 | 26 | 34 | 43 | 51 | 54 | 56 | 57 | 68 | 70 |
| Danish designation | 1 | 2 | 3 | 4 | 5 | 8 | 9N | 12F | 14 | 17F | 19F | 20 | 22F | 23F | 25 | 6B | 10A | 11A | 7F | 15B | 18C | 19A | 9V | 33F |

In another particular embodiment, the antigen is a bacterial CPS derived from *S. pneumoniae* serotypes 1, 3, 4, 5, 6B, 9V, 14, 18C, 19F and 23F. In another particular embodiment, the *S. pneumoniae* CPS is a *S. pneumoniae* CPS type 4 (PS4). In another particular embodiment, the *S. pneumoniae* CPS is a *S. pneumoniae* CPS type 3 (PS3).

In another particular embodiment, the antigen is a *Neisseria meningitidis* (*N. meningitidis*) antigen, e.g. a *N. meningitidis* protein, peptide or CPS. In further particular embodiments, the *N. meningitidis* CPS includes, but is not limited to, CPS derived from *N. meningitidis* Group A, B, C, W-135 and Y. In another particular embodiment, said *N. meningitidis* CPS is a *N. meningitidis* group B CPS (MnB). In another particular embodiment, said *N. meningitidis* CPS is a *N. meningitidis* group C CPS (MnC).

As can be appreciated by those of skill in the art, the actual number of peptide units per antigen in a population of conjugates formed via conventional chemical conjugation methods varies from molecule to molecule within the population. The multimeric carriers of the invention and the conjugates and compositions comprising them are thus understood to be characterized by at least 30 covalently attached units of p458 or analogs and derivatives thereof in average per molecule. In another embodiment, said conjugates have a molar ratio of peptide to antigen that is greater than about 30:1, preferably greater than about 40:1, 50:1, 60:1, 70:1, 80:1, 90:1, 100:1, or 200:1. Non-limitative examples for assessing the average peptide/carbohydrate ratio in a population of conjugates comprising a polysaccharide antigen and a peptide carrier are presented in the Examples section hereinbelow.

Advantageously, a conjugate of a bacterial CPS of about 50-100 kDa, such as meningococcal and pneumococcal CPS, attached to a multimeric p458 carrier of the invention has an average peptide/polysaccharide ratio (w/w) of at least 1:1, preferably at least 1.3:1 and more preferably at least 1.5:1, 2:1, 4:1, or, in other embodiments, 6:1 or 8:1.

According to currently preferred embodiments, a conjugate of a bacterial CPS of about 50-100 kDa and a peptide carrier of the invention has a molar ratio of peptide to antigen of between about 50:1 and about 200:1, or a weight ratio of between about 1.5:1 and about 6:1.

Certain non-limitative examples for chemically conjugating bacterial CPS to the p458 carriers of the invention are presented in the Examples below. This as well as other conjugation methods known in the art may be utilized in accordance with the present invention, as long as the required peptide/antigen ratio is maintained in the administered composition. For example, alternate methods for conjugating bacterial CPS to various carriers are described in U.S. Pat. Nos. 5,736,146, 7,018,637 and 5,565,204.

Other exemplary peptide-polysaccharide conjugation methods which may be utilized in accordance with certain embodiments of the present invention are cyanogen bromide-based methods as described, for example, in Kohn and Wilchek (1982), and Schneerson, et al. (1980).

In certain other particular embodiments, for example, multimeric p458 carriers comprising multiple copies of the carrier peptide in tandem are synthesized, and conjugated to the antigen in order to provide a high peptide/antigen ratio. For instance, a carrier comprising two p458h peptides in tandem has an amino acid sequence as set forth in SEQ ID NO:7, as follows: NEDQKIGIEIIKRTLINEDQKIGIEIIKRTLKI.

In certain embodiments, for the production of carriers comprising multiple repeats of the peptide, recombinant methods well known in the art are conveniently employed (see, e.g. Sambrook et al., 2001). Typically, a DNA molecule encoding a p458 peptide carrier is linked, in frame, to additional DNA molecules encoding the peptide carrier. The encoded peptide or polypeptide comprises multiple peptide units, which may be linked directly or via a linker. The chimeric DNA construct, along with suitable regulatory elements can be cloned into an expression vector and expressed in a suitable host. Accordingly, the present invention further encompasses the recombinant DNA, a recombinant expression vector comprising the recombinant DNA and a host cell comprising the recombinant expression vector. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Moreover, polynucleotides that include more or less nucleotides can result in the same or equivalent proteins.

A variety of expression vector/host systems may be utilized to contain and express sequences encoding the fusion proteins of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed. The expression of the construct according to the present invention within the host cell may be transient or it may be stably integrated in the genome thereof.

Host cells transformed with nucleotide sequences encoding a fusion protein of the invention may be cultured under conditions suitable for the expression and recovery of the protein from cell culture. The protein produced by a transformed cell may be secreted or contained intracellularly depending on the sequence and/or the vector used. The fusion protein may also be designed to include a purification facilitating domain, optionally linked to the fusion protein via a cleavable linker sequence, such as those specific for Factor XA or enterokinase (Invitrogen, San Diego, Calif.). Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.).

Another method for enhancing the peptide/antigen ratio is by forming a branched peptide carrier or a dendrimer of carrier peptide units, using e.g. lysine branching agents (see U.S. Pat. No. 7,018,637). For example, peptides can be linked via the multiple antigenic peptide system (see, e.g., U.S. Pat. No. 5,229,490). The multiple antigen peptide system makes use of multifunctional core molecules (e.g., lysines), where each of the functional groups on the core molecule forms at least two branches, the principal units of which are also multifunctional. Each multifunctional unit in a branch provides a base for added growth, resulting in exponential growth of the dendritic polymer. Peptides are then joined to the dendritic core using a linking molecule (e.g., glycine). The multiple antigen peptide system links a large number of synthetic peptides to the functional group of a dendritic core molecule providing a high concentration of synthetic peptides in a low molecular volume. Additionally, similar or different synthetic peptides can be linked by controlled polymerization through derivatization of the amino-terminus of a peptide with the acryloyl ($CH_2$=CH—) group using acryloyl chloride. The derivatized peptides are then polymerized singly or in admixture with similarly derivatized peptides by free radical initiation of chain elongation. As a result, peptides are assembled into polymers in which the peptide determinants form side chains pendant from an alkane backbone.

Vaccine Compositions and Methods Thereof.

The immunogenic conjugates of the invention may be formulated with one or more pharmaceutically acceptable excipients and optionally other ingredients. The pharmaceutically acceptable excipient(s) must be "acceptable" in the sense of being compatible with the other ingredients of the formulation and not deleterious to the recipient thereof. The formulations may conveniently be presented in unit dosage form and may be prepared by any method well known in the pharmaceutical art.

In another aspect, the invention provides a vaccine composition comprising at least one multimeric carrier in admixture with at least one antigen, and a pharmaceutically acceptable carrier, excipient or diluent, as detailed herein.

Compositions of the invention can include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular, intraperitoneal or intravenous administration (e.g., injectable administration), such as sterile suspensions or emulsions.

In certain embodiments, intravenous and parenteral administration are preferred. Such compositions may be in admixture with a suitable carrier, diluent, or excipient such as sterile water, physiological saline, glucose, dextrose, glycerol, ethanol or the like and combinations thereof. Typically, such vaccines are prepared as injectables either as liquid solutions or suspensions; solid forms suitable for solution in, or suspension in, liquid prior to injection may also be prepared. The preparation may also be emulsified or lyophilized.

Additional formulations that are suitable for other modes of administration include, but are not limited to, suppositories and oral formulations. For suppositories, traditional binders and carriers may include, for example, polyalkalene glycols or triglycerides. Oral formulations include such normally employed excipients as, for example, pharmaceutical grades of mannitol, cellulose, magnesium carbonate and the like. These compositions take the form of solutions, suspensions, tablets, pills, capsules, sustained release formulations or powders.

The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", incorporated herein by reference, may be consulted to prepare suitable preparations, without undue experimentation.

In certain preferable embodiments, the vaccine compositions of the invention do not comprise an additional adjuvant.

In alternate embodiments, the vaccine compositions of the invention may further comprise a pharmaceutically acceptable adjuvant, including, but not limited to, vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'—N'bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions (including, but not limited to, oil-in-water emulsions having oil droplets in the submicron range, such as those disclosed by U.S. Pat. Nos. 5,961,970, 4,073,943 and 4,168,308); liposaccharides such as MPL® and mineral gels. The conjugates of this invention can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed.

The vaccine compositions of the present invention can be administered as a single dose or in a series (i.e., with a "booster" or "boosters"). Suitable regimes for initial administration and booster shots are also variable. In certain embodiments, regimes are typified by an initial administration followed in one or two week intervals by a subsequent injection or other administration. Alternatively, by means of a non-limitative example, a child could be vaccinated (by a single dose or several doses e.g. as described above) early in life, then be administered a booster dose up to ten years later.

The vaccines can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration, according to protocols well known in the art. The particular dosage of the conjugate antigen will depend upon the age, weight and medical condition of the subject to be treated, as well as on the identity of the antigen and the method of administration. Suitable doses will be readily determined by the skilled artisan. A preferred dose for human intramuscular, subcutaneous and oral vaccination (e.g. of a multimeric p458 conjugate comprising a polysaccharide antigen) is between about 0.1 and about 1000 µg of the conjugate. Adjustment and manipulation of established dosage ranges used with traditional carrier antigens for adaptation to the present vaccine is well within the ability of those skilled in the art.

The vaccine compositions of the invention may comprise one or more different antigens, e.g. CPS derived from a single bacterial strain or serotype or from multiple bacterial strains or serotypes. For example, without limitation, the vaccine may comprise a combination of CPS derived from *S. pneumoniae* serotypes 1, 2, 3, 4, 5, 6B, 7F, 8, 9N, 9V, 10A, 11A, 12F, 14, 15B, 17F, 18C, 19F, 19A, 20, 22F, 23F, and 33F, a combination of CPS derived from *S. pneumoniae* serotypes 1, 3, 4, 5, 6B, 9V, 14, 18C, 19F and 23F, or a combination of CPS derived from *S. pneumoniae* serotypes 4, 6B, 9V, 14, 18C, 19F and 23F.

According to another aspect, the present invention is directed to vaccine compositions comprising at least one conjugate, the conjugate comprising a capsular polysaccharide of *Neisseria meningitidis* group B (MnB) covalently attached to a multimeric carrier, in which the carrier comprises a plurality of peptide units comprising HSP60-derived sequences selected from the group of peptides consisting of:

(a) NEDQKIGIEIIKRTLKI,  (p458h; SEQ ID NO: 1)

(b) NEDQKIGIEIIKRALKI,  (p458; SEQ ID NO: 2)

(c) EGDEATGANIVKVALEA,  (p458mt; SEQ ID NO: 3)

(d) NEDQNVGIKVALRAMEA,  (p458e; SEQ ID NO: 4)

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo;
and a pharmaceutically acceptable carrier, adjuvant, excipient or diluent, wherein the vaccine compositions comprise between about 0.1 and about 1000 µg of the conjugate, preferably between about 0.1 and about 100 µg of said conjugate, and more preferably between about 0.2 and about 25 µg of said conjugate.

Preferably, the conjugate comprises at least about 30, preferably at least about 40, more preferably at least about 50 copies of the peptide carrier. In certain currently preferred embodiments, said conjugate comprises between about 30 and about 200 peptide copies of the peptide carrier, preferably between about 40 and about 100 or about 50 and about 80 copies of the peptide carrier.

In another embodiment, the vaccine composition further comprises a second conjugate, the second conjugate comprising a capsular polysaccharide of *Neisseria meningitidis* group C (MnC) covalently attached to a multimeric carrier, in which the carrier comprises a plurality of peptide units comprising HSP60-derived sequences selected from the group of peptides consisting of:

(a) NEDQKIGIEIIKRTLKI,  (p458h; SEQ ID NO: 1)

(b) NEDQKIGIEIIKRALKI,  (p458; SEQ ID NO: 2)

```
(c) EGDEATGANIVKVALEA,    (p458mt; SEQ ID NO: 3)

(d) NEDQNVGIKVALRAMEA,    (p458e; SEQ ID NO: 4)
```

(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the capsular polysaccharide when the conjugate is administered in vivo;
and a pharmaceutically acceptable carrier, adjuvant, excipient or diluent.

Preferably, the conjugate comprises at least about 30, preferably at least about 40, more preferably at least about 50 peptide carriers. In certain currently preferred embodiments, said conjugate comprises between about 30 and about 200 peptide carriers, preferably between about 40 and about 100 or between about 50 and about 80 peptide carriers.

In other embodiments, a suitable dose range for the MnC conjugates of the invention is between about 10 and about 1000 μg of the conjugate, preferably between about 20 and about 500 μg of the conjugate, and more preferably between about 40 and about 250 μg of the conjugate.

In another aspect, there is provided a method for enhancing the immunogenicity of an antigen comprising conjugating the antigen to a plurality of peptide units comprising HSP60-derived sequences, in which each peptide unit is selected from the group of peptides consisting of:

```
(a) NEDQKIGIEIIKRTLKI,    (p458h; SEQ ID NO: 1)

(b) NEDQKIGIEIIKRALKI,    (p458; SEQ ID NO: 2)

(c) EGDEATGANIVKVALEA,    (p458mt; SEQ ID NO: 3)

(d) NEDQNVGIKVALRAMEA,    (p458e; SEQ ID NO: 4)
```

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;
wherein the antigen is conjugated to at least about 30 peptide units;
with the proviso that said antigen is other than the capsular polysaccharide (CPS) Vi of *Salmonella typhi*.

Other embodiments of the present invention are directed to the use of vaccines comprising the conjugates and multimeric carriers of the invention for the preparation of a medicament. In various embodiments, the medicament is useful for immunizing a subject in need thereof, for preventing bacterial infection, and for treating cancer and inhibiting tumor progression, as detailed herein.

By the term "immunizing a subject" is meant administering to the subject a composition of the invention, in an amount effective to elicit or enhance a beneficial immune response in said subject (e.g. administration of an antigen-carrier conjugate of the invention elicits an immune response against the antigen, and subsequently provides enhanced protection against the pathogen from which said antigen is derived). While this disclosure generally discusses immunization in the context of prophylactic methods of protection, the term "immunizing" is meant to refer to both prophylactic and therapeutic methods. Accordingly, the present invention may be used as a vaccine for prophylactic protection or in a therapeutic manner; that is, as immunotherapeutic methods and preparations.

In another aspect, there is provided a method for immunizing a subject in need thereof, comprising administering to the subject an effective amount of a vaccine composition of the invention, as detailed herein. In one embodiment, the vaccine comprises a multimeric p458 carrier of the invention conjugated to, or in admixture with, an antigen. In another embodiment, the vaccine comprises a Ec27 carrier of the invention conjugated to, or in admixture with, an antigen.

In another aspect, the invention provides a method for immunizing a subject in need thereof against *Neisseria meninigitidis* infection, comprising the step of administering to the subject a prophylactically effective amount of a vaccine composition comprising at least one conjugate, the conjugate comprising a capsular polysaccharide of *Neisseria meningitidis* group B (MnB) covalently attached to a p458 carrier of the invention.

In another aspect, the invention provides a method for immunizing a subject in need thereof against *Neisseria meningitidis* infection, comprising the step of administering to the subject a prophylactically effective amount of a vaccine composition comprising at least one conjugate, the conjugate comprising a capsular polysaccharide of *Neisseria meningitidis* group B (MnB) covalently attached to a Ec27 carrier of the invention.

In another aspect, the invention provides a method of treating cancer in a subject in need thereof, comprising the step of administering to the subject a therapeutically effective amount of a vaccine composition comprising at least one conjugate, the conjugate comprising a capsular polysaccharide of *Neisseria meningitidis* group B (MnB) covalently attached to a p458 carrier of the invention.

In another aspect, the invention provides a method of treating cancer in a subject in need thereof, comprising the step of administering to the subject a therapeutically effective amount of a vaccine composition comprising at least one conjugate, the conjugate comprising a capsular polysaccharide of *Neisseria meningitidis* group B (MnB) covalently attached to a Ec27 carrier of the invention.

In another embodiment the tumor is a α(2-8) polysialic acid expressing tumor including, but not limited to malignancies of neuroectodermal origin (e.g. small cell lung cancer), neuroblastoma, thyroid carcinoma, primary C-cell hyperplasia, rhabdomyosarcoma, natural killer cell derived-lymphoma, and Wilm's tumor.

In another aspect, the invention provides a method of inhibiting tumor metastasis in a subject in need thereof, comprising the step of administering to the subject a therapeutically effective amount of a vaccine composition comprising at least one conjugate, the conjugate comprising a capsular polysaccharide of *Neisseria meningitidis* group B (MnB) covalently attached to a p458 carrier of the invention.

As used herein, "treating" cancer (or treating a subject with cancer) refers to taking steps to obtain beneficial or desired results, including but not limited to, alleviation or amelioration of one or more symptoms of the cancer, diminishment of extent of disease, delay or slowing of disease progression, amelioration, palliation or stabilization of the disease state, partial or complete remission, prolonged survival and other beneficial results known in the art.

In another aspect, the invention provides a method of inhibiting tumor metastasis in a subject in need thereof, comprising the step of administering to the subject a therapeutically effective amount of a vaccine composition comprising at least one conjugate, the conjugate comprising a capsular polysaccharide of *Neisseria meningitidis* group B (MnB) covalently attached to a Ec27 carrier of the invention.

Cell Vaccines and Related Methods

In another aspect, the invention encompasses cell vaccines comprising antigen presenting cells (APC) loaded with the immunogenic conjugates of the invention.

According to this aspect, such cell vaccines preferably include cell vaccines in which allogeneic (i.e., cells derived from a source other than a patient, but that are histocompatible with the patient) or autologous (i.e., cells isolated from a patient) cells are exposed to a multimeric carrier-antigen conjugate contained in a therapeutic composition, and administered to a patient by, for example, intradermal, intravenous or subcutaneous injection.

Such APC are capable of presenting a peptide of the invention in the form of antigen-MHC class II complex, in a manner recognizable by specific effector cells of the immune system and thereby inducing an effective cellular immune response against the antigen being presented. Suitable cell populations may be e.g. peripheral blood mononuclear cells and APC purified therefrom such as macrophages, B-cells and dendritic cells. In some embodiments, dendritic cells are preferred; these cells may be classified into subgroups, including, e.g., follicular dendritic cells, Langerhans dendritic cells, and epidermal dendritic cells.

In one embodiment, the patient is human.

In another aspect, the invention provides a cell vaccine composition comprising APC exposed in culture, under conditions promoting uptake and processing of an antigen, to a conjugate comprising an antigen covalently attached to a multimeric carrier, in which the carrier comprises a plurality of peptide units comprising HSP60-derived sequences selected from the group of peptides consisting of:

(a) NEDQKIGIEIIKRTLKI,   (p458h; SEQ ID NO: 1)

(b) NEDQKIGIEIIKRALKI,   (p458; SEQ ID NO: 2)

(c) EGDEATGANIVKVALEA,   (p458mt; SEQ ID NO: 3)

(d) NEDQNVGIKVALRAMEA,   (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises at least about 30 peptide units per antigen molecule, to provide antigen-expressing APC.

In another aspect, the invention provides a method of stimulating an immune response in a subject in need thereof, comprising the steps of:

(a) obtaining antigen presenting cells (APC) from the subject, or from a donor histocompatible with said subject;

(b) exposing the APC in culture, under conditions promoting uptake and processing of an antigen, to a conjugate of the invention, to provide antigen-expressing APC; and (c) administering the antigen-expressing APC to said subject.

Optionally, the APC may be attenuated prior to their administration to the subject. Treatment to attenuate the APC may include, but is not limited to, gamma- or X-irradiation, or treatment with mitomycin C, by methods well known in the art. In one particular embodiment, the cells are attenuated by exposure to gamma irradiation (2000-10000 rads). In certain particular embodiments, use of attenuated APC may be preferred, for example, when the MHC compatibility between the APC and the recipient subject is partial. Certain non-limiting examples for APC attenuation are provided in the Examples section below.

Dendritic cells can be obtained by isolating dendritic precursor cells and inducing them to differentiate into dendritic cells, using methods well known in the art. Alternatively, dendritic cells may be isolated from both lymphoid and non-lymphoid tissues; typically they are purified from peripheral blood. Methods for isolation of human dendritic cells from blood include apheresis followed by procedures involving density gradient methods, positive selection (e.g., affinity chromatography with antibodies directed to dendritic cells surface markers), negative selection, or combinations thereof (see, e.g., WO97122349; WO95134638; WO98/01538; WO94/02156).

Dendritic cells may be isolated from a normal human or from a patient suffering from a disease. In either case, individuals may be treated with colony stimulating factors to increase their number of dendritic cells prior to isolation. For example, GM-CSF, may be infused into an individual at 250 µg/m$^2$/day for several days up to three weeks intravenously prior to obtaining the peripheral blood mononuclear leukocytes (PBML) for the purification of dendritic cells. This procedure may increase the yield of dendritic cells for antigen pulsing and subsequent administration.

The amount of conjugate used for pulsing APC will depend on the nature, size and purity of the conjugate. Typically, from about 0.05 µg/ml to about 1 mg/ml, most often from about 1 to about 100 µg/ml of an antigen such as a conjugate comprising a multimeric p458 carrier of the invention and a bacterial CPS is used. After adding the conjugate to the cultured APC, the cells are then allowed sufficient time to take up and process the antigen and express antigen peptides on the cell surface in association with MHC. Typically this occurs in about 18-30 hours, most often about 24 hours. A non-limitative example for pulsing APC with a conjugate of the invention is presented in the Examples herein.

The cells are administered in any suitable manner, preferably with a pharmaceutically acceptable carrier (e.g., saline). Usually administration will be intravenous, but intra-articular, intramuscular, intradermal, intraperitoneal, and subcutaneous routes are also acceptable. Administration (i.e., immunization) may be repeated at time intervals. Infusions of dendritic cells may be combined with administration of cytokines that act to maintain dendritic cells number and activity (e.g., GM-CSF, IL-12).

The dose administered to a patient, in the context of the present invention should be sufficient to induce an immune response as detected by assays which measure e.g. T cell proliferation, Ab production and/or effect a beneficial therapeutic response in the patient over time, e.g., to prevent infection of the pathogen or inhibit growth of cancer cells or result in reduction in the number of cancer cells or the size of a tumor. Typically, 105 to 109 or more antigen-expressing APC are infused, if available, or in other embodiments 106 to 107 antigen-expressing APC.

The following examples are presented in order to more fully illustrate some embodiments of the invention. They should, in no way be construed, however, as limiting the broad scope of the invention.

EXAMPLES

A. Pneumococcal Vaccines

Materials and Methods

Mice

Female BALB/c mice were purchased from Harlan Olac (Bicester, UK). Female C3HeB/Fej and C3H/Hej were obtained from the Jackson Laboratory. All mice were used at the age of 8-10 wk. The mice were maintained in a specific pathogen-free facility and were used according to the guidelines and under the supervision of the Animal Welfare Committee.

Isolation of Peritoneal Macrophages

Mice were injected i.p with 1 ml of Thioglycolate 3% (Difco, Detroit, Mich.). After 4 days, the peritoneum was washed with 10 ml ice-cold PBS. The cells were incubated on 24-well plate with full medium: DMEM (Gibco/BRL, Gaithersburg, Md.) containing 10% FCS (HyClone, Logan, Utah), 100 U/ml penicillin, 100 U/ml streptomycin, 2 mM L-glutamine, 1 mM sodium pyruvate and non-essential amino acids for 3 hours at 37° C., 5% $CO_2$. The non-adherent cells were removed.

Cell Lines

RAW 264.7 is a tumor macrophage cell line derived from BALB/c mice that retains its phagocytic and presenting capabilities. 4T1 is a breast cancer carcinoma cell line derived from BALB/c mice. Both cell lines were obtained from American Type Culture Collection (ATCC, Manassas, Va.) and were raised at 37° C., 5% $CO_2$ in a full medium.

Reagents

Reagents were PS4 (ATCC), LPS *Salmonella* minnesota polymyxin B (PmB), Gluteraldehide (GH), Paraformaldehide (PFA) (Merck, Darmstadt, Germany), Cytochalasin D (CytD), Dextran, Fluorescein Isothiocyanate (FITC) (Sigma-aldrich, Rehovot, Israel).

Peptides

Peptides were synthesized using a peptide synthesizer (Abimed model AMS 422; Langenfeld, Germany), according to the company's instructions for N-α-fluorenylmethoxycarbonyl synthesis. Peptide purity was determined by reversed-phase HPLC and by amino acid analysis. Peptide p458 was derived from murine HSP60, positions 458-474: NEDQKIGIEIIKRALKI. Peptide p30 was derived from Tetanus Toxoid (TT) protein, positions 947-967: FNNFTVSFWLRVPKVSASHLE.

PS4 Conjugation

PS4 dissolved in DDW (5 mg/ml) was activated with 0.1 ml of cyanogen bromide (20 mg/ml in acetone) in the presence of 30 mM triethylamine (Aldrich, Milwaukee, Wis.) in acetone at pH 7. After two minutes, 6-aminohexanoic acid (10 mg/ml in DDW) was added for 2 h of incubation at 4° C. We then added 12 mg of 1-(3-dimethylaminopropyl)-3-ethylcarbodiimide hydrochloride (CDI) (Aldrich; Milwaukee, Wis., USA) and 7 mg of the peptide to the solution. The pH was adjusted to 6 at room temperature. Four hours later, 12 mg of CDI was again added, the mixture was incubated overnight and then dialyzed at 4° C. against DDW.

IL-12 Cytokine Determination

The presence of IL-12 in culture supernatants were determined by ELISA for IL-12 (OptiEIA kits; BD Pharmingen, San Diego, Calif.) following the manufacturer's instructions using Maxisorb 96-well plates. Standard curves were established using mouse recombinant IL-12.

Preparation of Column-Purified Mouse Anti-PS4 Polyclonal Abs

Female BALB/c mice were immunized three times with PS4-p458 conjugate (2 µg/mouse; ~1:1 PS4 to p458) emulsified in IFA at two weeks intervals. Serum was collected after three weeks from the last injection. Anti-PS4 antibodies were purified by affinity chromatography:PS4, activated by cyanogen bromide, was coupled to 1.6 diaminohexan-sepharose (kindly provided by Prof. M. Wilchek of the Weizmann Institute of Science, Israel). The serum was loaded on the column and the effluent was collected. The column was washed with 10 volumes of PBS and the anti-PS4 antibodies were eluted with 0.1M acetic acid, pH 3, and neutralized immediately with 1M Tris pH 10. The elution was tested for specificity in ELISA against the PS4. The purified anti-PS4 Ab was used in the flow cytometry and immunocytochemistry assays.

Flow Cytometric Analysis

Expression of PS4 on the macrophage surface was determined by flow cytometry. RAW cells or peritoneal macrophages ($1×10^6$/per tube) were pulsed with the conjugates or with PS4 alone as indicated in the text. The cells were washed with PBS/0.5% BSA and fixed with 1% PFA. The cells were then incubated for 30 min with Ab to the anti-FcγRIII/II 2.4G2 (BD Pharmingen) to block nonspecific binding. After washing, the cells were incubated with the column-purified mouse anti-PS4 Abs for 45 minutes in ice. After washing, FITC-conjugated goat anti-mouse IgG secondary Ab (Jackson Immunoresearch Laboratories, West Grove, Pa.) was added for an additional 45 minutes in ice. Flow cytometry analysis was done by FACSort (BD Biosciences) and CellQuest software (BD Biosciences).

PS4 Labeling with FITC

PS4 was dissolved in of DDW (10 mg/ml). Then, 15 mg (0.1 mmol) of 1,3-diaminopropane di-hydrochloride dissolved in DDW was added. N-ethyl-N'-(3-dimethylaminopropyl)-carbodiimide (EDC.HCL) (19 mg; 0.1 mmol) (Sigma-Aldrich) was then added, and the reaction mixture was kept for 4 hours at room temperature. Then another portion of EDC.HCL (9.5 mg; 0.05 mmol) was added. After 10 hours at room temperature, the clear homogenous reaction mixture was extensively dialyzed against 0.1N acetic acid at 4° C. to remove low-molecular weight molecules. The pH was adjusted to 7.5 with 0.1N $KHCO_3$ solution followed by the addition of FITC (19 mg; ~0.05 mmol). After standing overnight at room temperature, the yellowish solution was dialyzed extensively against 0.1N acetic acid at 4° C. The solution was divided to aliquots and frozen at −20° C.

Immunocytochemistry

RAW cells were cultured in a full medium on 10 mm glass cover-slips (Deckglaser, Germany) in 24-well plates ($2×10^5$/well) overnight at 37° C. The cells were pulsed with conjugates or with PS4 alone, as indicated in the text. Then, the cells were washed and fixed with 1% PFA for 20 minutes at room temperature. After washing, the cells were incubated with the column-purified mouse anti-PS4 Ab for 45 minutes at room temperature, washed with PBS twice and incubated with FITC-conjugated goat anti-mouse IgG secondary Ab (Jackson Immunoresearch Laboratories) for an additional 45 minutes at room temperature. In some experiments we used FITC-labeled PS4 and the membranes were stained using anti-H-$2D^d$ Ab (clone #3458 was kindly provided by Prof Lea Eisenbach, Weizmann Institute of Science), then, biotinylated affinity purified anti-mouse IgG secondary Ab (BioMakor, Rehovot, Israel) and finally, cy5-streptavidin (Jackson ImmunoReasearch).

Immunization with Pulsed-Macrophages

RAW cells were cultured on 10 cm tissue culture plates ($5\times10^6$/plate) in full medium. The day after, the cells were pulsed with the conjugates or the PS4 alone for different time periods, as indicated in the text. Then, the cells were harvested and extensively washed with ice-cold PBS to remove unbound PS4. Then, the cells were irradiated with 5000 RAD and injected i.p to naïve female BALB/c mice.

Pn Type 4 Bacteria

Lyophilized Pn bacteria type 4 and PS4 Ag were obtained from the ATCC. Pn bacteria were reconstituted and subcultured on sheep's blood agar (Hy Laboratories, Rehovot, Israel) and the colonies were resuspended in brain-heart infusion (BHI) broth (Hy Laboratories). After 6 h, the bacterial cultures were aliquoted and stored at $-80°$ C. in medium with 25% glycerol. For pneumococcal challenge, a frozen aliquot of Pn bacteria was thawed in BHI broth and was grown for 6 h at $37°$ C., and then transferred to ice until injection. Bacterial growth was estimated by the level of turbidity using an O.D reader at 545 nm. The actual dose of viable bacteria injected in each challenge was determined by plating dilutions of the bacteria on sheep's blood agar for 24 h at $37°$ C. and counting the number of CFU. Pneumococcal virulence was obtained by periodic passage in mice: mice were injected with 100 Pn CFU, and 20 h later the spleens were harvested, passed through a wire mesh, and seeded on sheep's blood agar. The bacteria were then prepared as indicated above.

Determination of Minimal Lethal Dose Following Pn Challenge

Naive BALB/c mice were injected i.p with 200 µl of serially diluted bacterial growth in BHI broth medium. The survival was determined daily for 2 wk. All naive mice challenged with two or more CFU died within 2 days of challenge. The minimal lethal dose that killed half of the challenged mice ($LD_{50}$) was determined to be one bacterium per mouse. The $LD_{50}$ determination was done with large numbers of mice.

Statistics

The InStat 2.01 program (GraphPad) was used for statistical analysis. Statistical analysis was performed using the two-sided Welch T test and Fisher's exact Chi test. Differences were considered statistically significant at $p<0.05$.

Example 1

The PS4-p458 Conjugate is Immunogenic in PBS

Figure 1B:
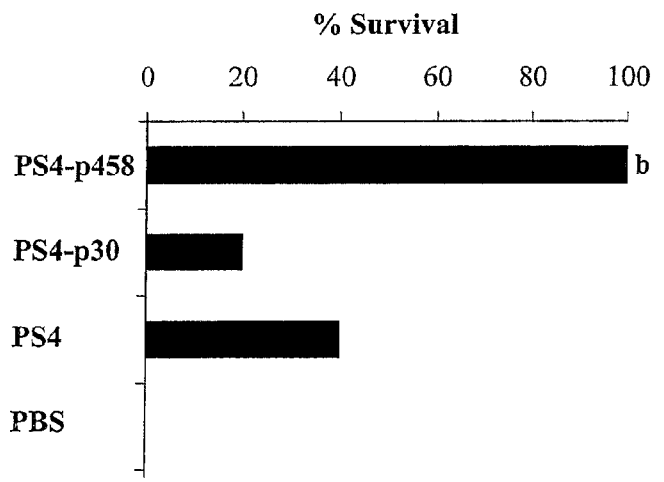

We previously reported that various conjugate vaccines of PS4 such as PS4-p458 and PS4 conjugated to a TT peptide, PS4-p30, were effective in inducing IgG anti-PS4 antibodies, and protected against lethal Pn challenge when the vaccine was administered in IFA (14); and see FIG. 1A. The use of adjuvants, however, can evoke undesirable side effects, and it would be important to develop effective vaccines that need not be injected with adjuvants. FIG. 1B shows that the PS4-p458 conjugate was effective in protecting mice against Pn challenge even when injected in PBS; the PS4-p30 conjugate, in contrast, was markedly less effective in PBS. Thus, the PS4-p458 conjugate is significantly more immunogenic than the PS4-p30 conjugate in PBS. This suggests that the PS4-p458 conjugate might have an intrinsic adjuvant-like effect.

In FIG. 1, [a] indicates $p<0.015$ compared to PS4, [b] indicates $p<0.01$ compared to PS4-p30 and PS4.

Example 2

The PS4-p458 Conjugate Stimulates a Macrophage Cell Line to Secrete IL-12

Figure 2:
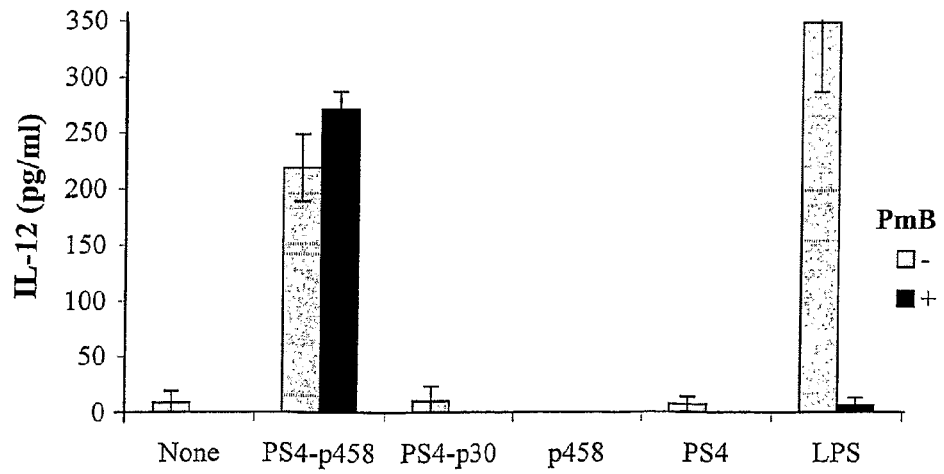

Adjuvant components are known to stimulate innate cells via TLR molecules to secrete pro-inflammatory cytokines such as TNFα and IL-12. To investigate whether the PS4-p458 conjugate has an adjuvant-like effect in vitro, we examined its ability to stimulate macrophages to secrete IL-12. A macrophage cell line (RAW 264.7) was pulsed for 24 hours with the PS4-p458 conjugate, the PS4-p30 conjugate, un-conjugated p458 peptide, un-conjugated PS4, or LPS. FIG. 2 shows that only the PS4-p458 conjugate and LPS induced the macrophage line to secrete IL-12; un-conjugated PS4 or p458 or the PS4-p30 conjugate failed to do so. The stimulatory effect of the PS4-p458 conjugate was not due to LPS contamination, since an LPS inhibitor, polymyxin B (PmB), annulled the effect of LPS but not that of the PS4-p458 conjugate. These findings suggest that the multivalent structure of the PS4-p458 conjugate has a stimulatory effect on macrophages that could not be elicited by the linear p458 peptide, PS4 or the PS4-p30 conjugate. The stimulatory effect of the PS4-p458 conjugate on macrophages could account for its effectiveness as a vaccine in PBS.

Example 3

Macrophages Activated by PS4-p458 Express Surface PS4 for a Prolonged Time

Figure 3:
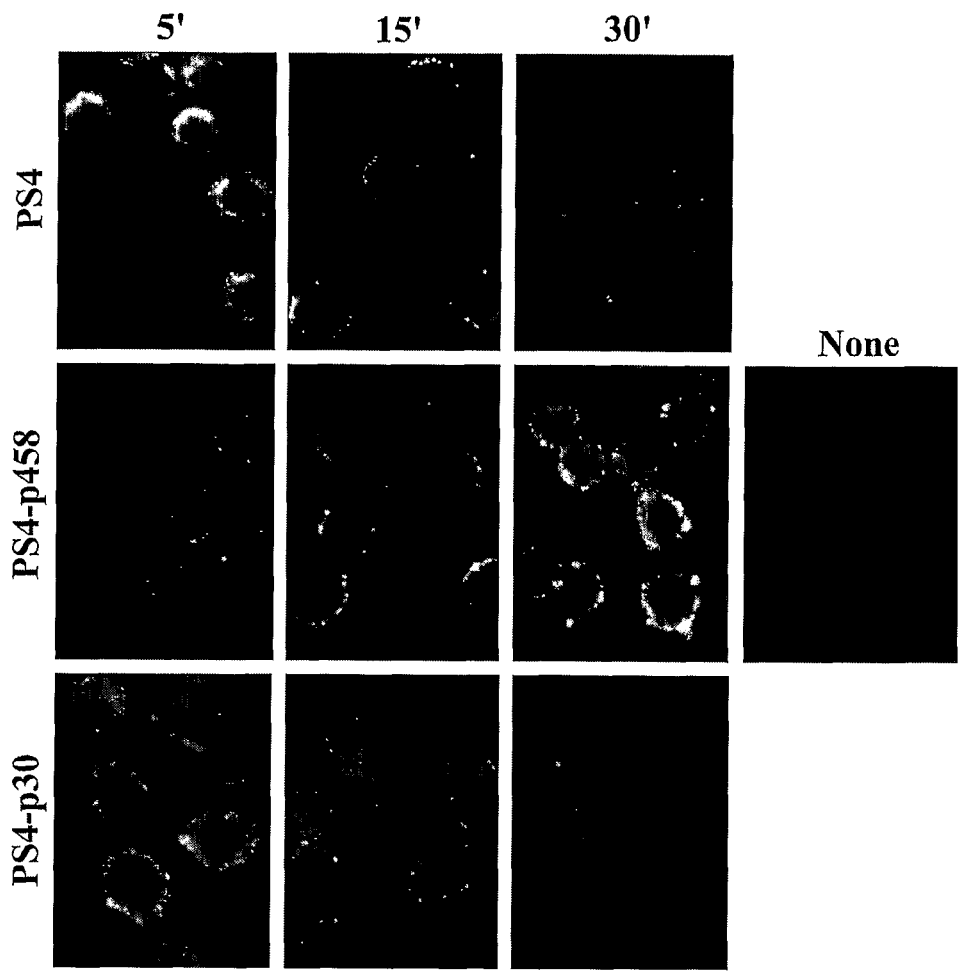

We examined whether the stimulatory effect of the PS4-p458 conjugate might influence the appearance of the PS4 moiety on the macrophage surface. RAW cells were incubated for 5, 15 or 30 minutes with the PS4-p458 conjugate, the PS4-p30 conjugate or with PS4 alone, then fixed and stained with FITC-conjugated anti-PS4 Abs. The surface expression of PS4 was detected using immuno-cytochemistry. FIG. 3 shows that surface expression of PS4 following pulsing with PS4-p30 or unconjugated PS4 was present at 5 minutes and deceased thereafter; in contrast, pulsing with the PS4-p458 conjugate led to the appearance of PS4 on the cell surface at 30 minutes.

Figure 4A:
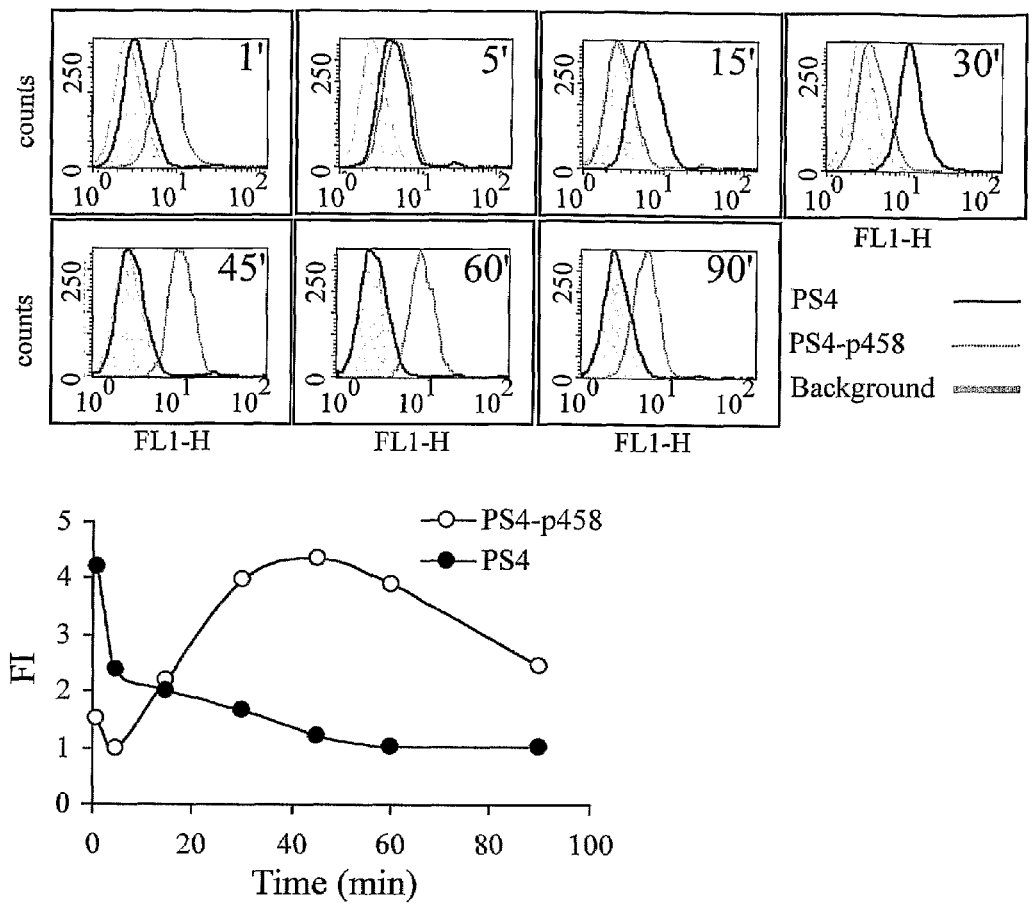

To examine the kinetics of PS4 expressed on the surface in more quantitative terms, we used flow cytometry. RAW cells were incubated with PS4-p458 or with un-conjugated PS4 for various time periods, then fixed and stained with FITC-conjugated anti-PS4 Ab. FIG. 4A shows that the expression of PS4 on the surface of PS4-pulsed macrophages decreased sharply within minutes and then gradually declined over the next hour. The appearance of PS4 on the surface of the PS4-p458-pulsed macrophages differed; PS4 continued to increase over 45 minutes, remained high for an hour, and then gradually decreased, but was still relatively high at 90 minutes. The PS4-p30 conjugate did not show this prolonged appearance of surface PS4 and behaved as did un-conjugated PS4. Thus the stimulatory effect of the PS4-p458 conjugate not only induced the macrophage line to secrete IL-12, it also led to the late and prolonged appearance of PS4 on the cell surface.

Example 4

Effects of the PS4-p458 Conjugate Depend on TLR-4 Signaling

Figure 4B:
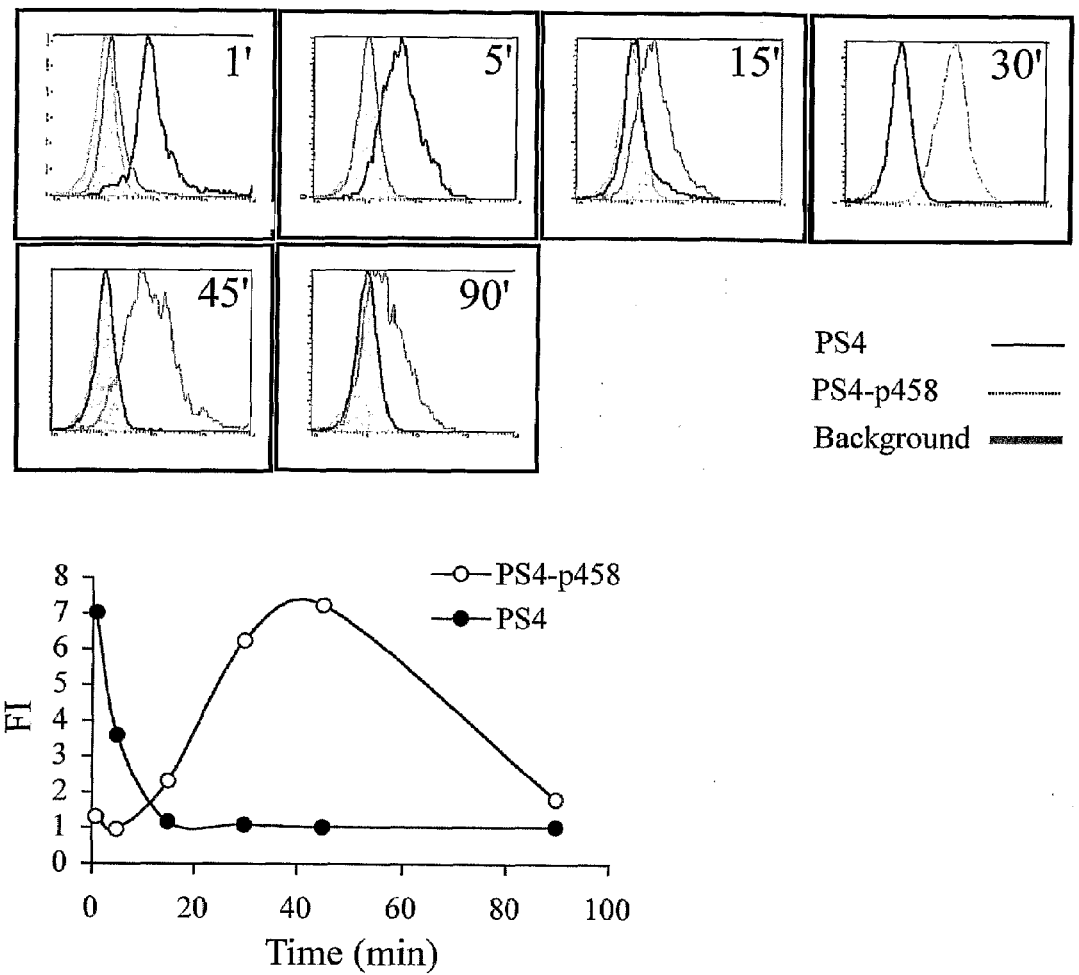
Figure 4C:
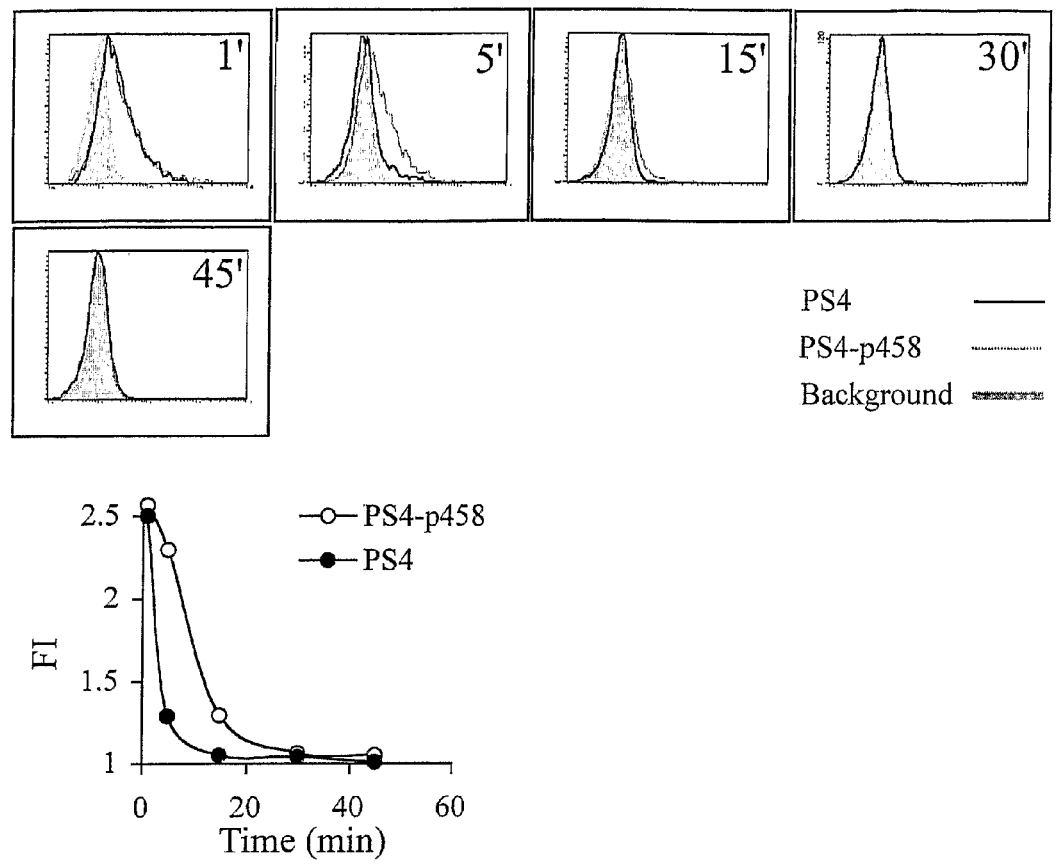

Since the p458 carrier originated from the HSP60 molecule, which has been reported to activate immune cells via TLR-4 (Cohen-Sfady et al., 2005) we tested whether the prolonged appearance of PS4 on the cell surface might also require functional TLR-4. We isolated peritoneal macrophages from wild-type C3H/HeB mice or from TLR-4-mutant C3H/HeJ mice, and repeated the assay for the detection of surface PS4 using anti-PS4 Ab, as we had done with the RAW cell line. FIGS. 4B and 4C show that the macrophages from the wild-type C3H/HeB mice also manifested a prolonged appearance of PS4 on the cell surface in response to the PS4-p458 conjugate. However, the TLR-4 mutant macrophages failed to do so: there was no difference in the appearance of PS4 in the TLR-4 mutant macrophages irrespective of whether they had been incubated with the PS4-p458 conjugate or with PS4 alone. These results suggest that the late, prolonged appearance of PS4 induced by the PS4-p458 conjugate is a process that is dependent on stimulation via intact TLR4. Moreover, the phenomenon is not limited to the RAW macrophage line, but can be induced by the PS4-p458 conjugate in primary peritoneal mouse macrophages.

Example 5

Macrophages Pulsed with PS4-p458 Induce Protection Against Lethal Challenge

We studied whether late-appearing, surface PS4 can induce resistance to Pn challenge. RAW cells were pulsed with PS4-p458, PS4-p30 or with un-conjugated PS4 for 30 minutes—a time when PS4 can be detected on the surface of the cells following incubation with the PS4-p458 conjugate but not after incubation with PS4-p30 or with un-conjugated PS4. The cells were irradiated to block their proliferation, and were injected i.p into naïve BALB/c mice. Three weeks later the mice were challenged with a lethal dose of Pn ($LD_{50} \times 1000$).

Figure 5:
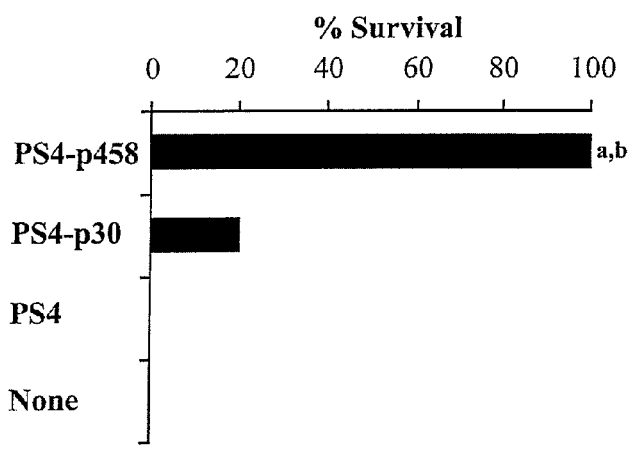

FIG. 5 shows that the mice that had been injected with the PS4-p458-pulsed macrophages were completely protected against the lethal Pn challenge. In contrast, the mice that had been injected with macrophages pulsed with the PS4-p30 conjugate or with un-conjugated PS4 were significantly less protected. Thus it appears that the PS4 present on the macrophage surface can induce protection against Pn challenge.

In FIG. 5, $^a$ indicates p<0.047 compared to PS4-p30; $^b$ indicates p<0.008 compared to PS4 and None.

Example 6

Figure 6A:
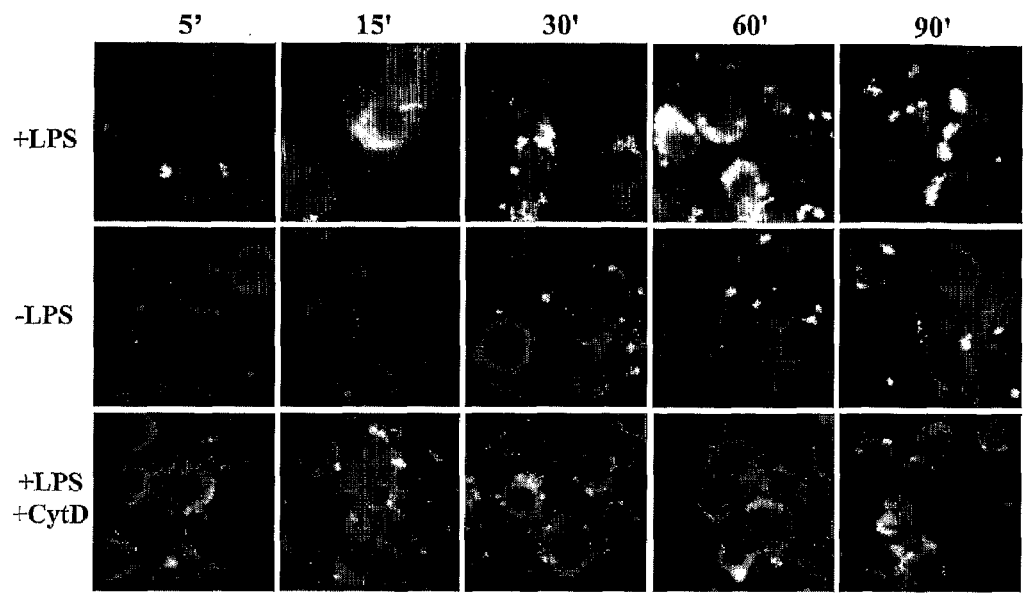
Figure 6B:
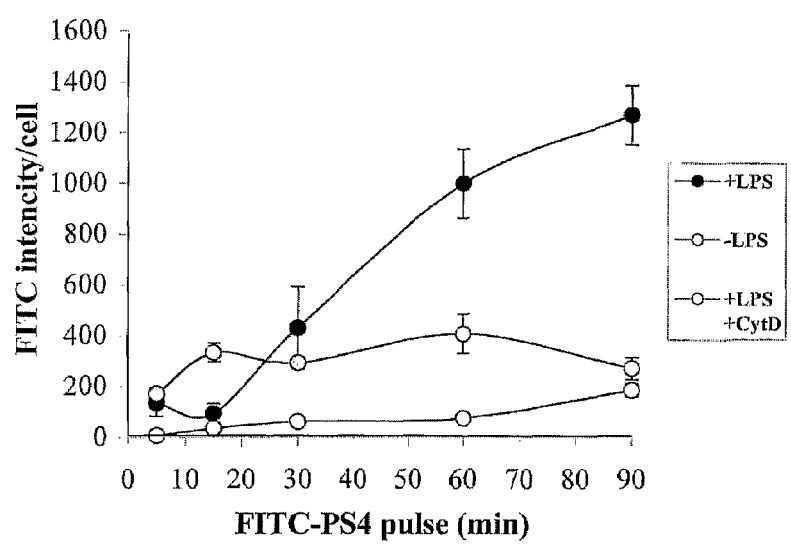

Pre-Stimulation with LPS Induces Prolonged Surface Expression of PS4 on Macrophages As described above (FIG. 4), the ability of the PS4-p458 conjugate to induce prolonged surface expression of PS4 on the macrophage surface depends on a functional TLR-4 molecule. If TLR-4 activation is sufficient as well as necessary for prolonged surface expression of PS4, then it should be possible to induce the effect using un-conjugated PS4 along with a known TLR-4 activator. To test this idea, RAW cells were pre-stimulated or not with bacterial LPS, a classic TLR-4 ligand, before incubating the cells with un-conjugated PS4. We used PS4 internally labeled with FITC to follow PS4 localization. FIG. 6A shows that RAW cells that had been pre-stimulated with LPS internalized the labeled PS4 within 15 minutes; the PS4 appeared to be inside the cells. From 30 to 90 minutes, however, the labeled PS4 molecules appeared on the cell surface, as clustered nodules. In contrast, the RAW cells that had not been pre-treated with LPS (FIG. 6A) manifested less PS4 at the cell surface. A quantitative analysis of FITC intensity on the cell surface is presented in FIG. 6B; the FITC intensity of the PS4 on the surface of LPS-treated macrophages decreased slightly after 15 minutes of incubation and then increased at 60 and 90 minutes. These results demonstrate that pre-stimulation with LPS can induce the prolonged appearance of PS4 on the cell surface following pulsing with un-conjugated PS4, similar to that observed following pulsing with the PS4-p458 conjugate (FIG. 4).

Endocytosis and exocytosis are processes that require cytoskeletal rearrangement and polymerization. We examined whether cytochalasin D (CytD), an inhibitor of cytoskeleton rearrangement, might affect the appearance of PS4 on the macrophage surface. Prior treatment with CytD indeed abrogated the late appearance of PS4 on the surface of LPS-stimulated RAW cells (FIG. 6A,B). Thus, the prolonged expression of surface PS4 following LPS stimulation would seem to require rearrangement of the cytoskeleton.

Example 7

The Specificity of FITC-Labeled PS4 Expression on the Surface is Specifically Blocked by Unlabeled PS4

Figure 7:
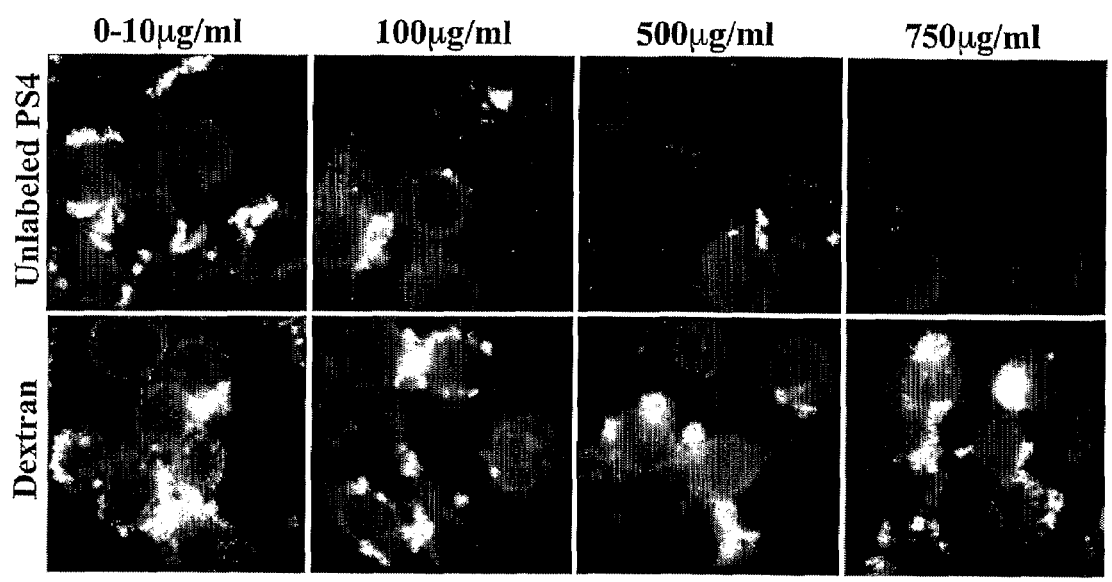

To investigate whether the late, prolonged appearance of PS4 at the macrophage surface involves a specific interaction of PS4 with the cell, we conducted competition experiments using unlabeled PS4 or dextran, an oligosaccharide of glucose with the same average molecular weight as PS4. RAW cells were pre-activated with LPS and then incubated with various amounts of unlabeled competitor for one hour, and then FITC-labeled PS4 was added for additional hour—at the time the unlabeled PS4 should be presented on the cell surface. The PS4 binding appeared to be specific (FIG. 7); the FITC-labeled PS4 at the cell surface was greatly inhibited by a 100-fold excess of unlabeled PS4, whereas pre-incubation with the same amount of dextran had no inhibitory effect. These results suggest that the PS4 appearing on the cell surface results from an interaction with a specific molecule or molecules, and is not the result of unspecific glycan binding.

Example 8

Figure 8A:
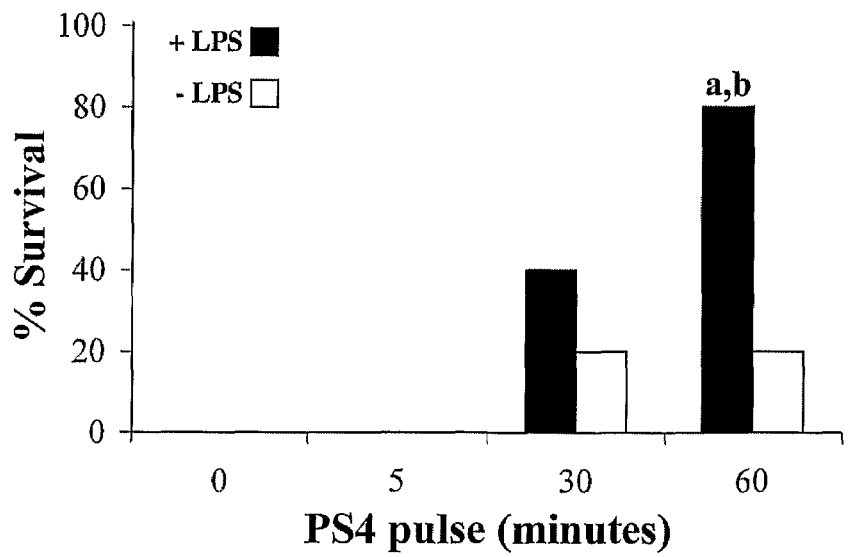

Macrophages Stimulated with LPS and Pulsed with P84 Induce Protection to Pn Challenge As seen above (FIG. 5), macrophages pulsed with the PS4-p458 conjugate induced protection to lethal Pn challenge. Accordingly, we examined whether the late appearance of PS4 following LPS stimulation is also able to induce functional resistance to lethal Pn challenge. Mice were injected with LPS-stimulated RAW cells that had been pulsed with PS4 for 5, 30 or 60 minutes; see the kinetics of the surface appearance of PS4 in FIG. 5. Three weeks later, the mice were challenged i.p with a lethal dose of Pn bacteria ($LD_{50} \times 100$). The RAW cells stimulated with LPS and pulsed with PS4 for 60 minutes induced significantly more protection than those pulsed with PS4 for only 5 or 30 minutes (FIG. 8A). PS4-pulsed macrophages that had not been treated with LPS were significantly less protective. These results indicate that the cell-induced protection to Pn challenge is associated with the presence of PS4 on the cell surface induced by LPS stimulation.

In FIG. 8A, $^a$ indicates p<0.01 compared to -LPS, 60 minutes; $^b$ indicates p<0.001 compared to 0.5 min. The graph summarizes three different experiments.

Example 9

Cell-Vaccinated Mice Clear Pn Bacteria Efficiently

Figure 8B:
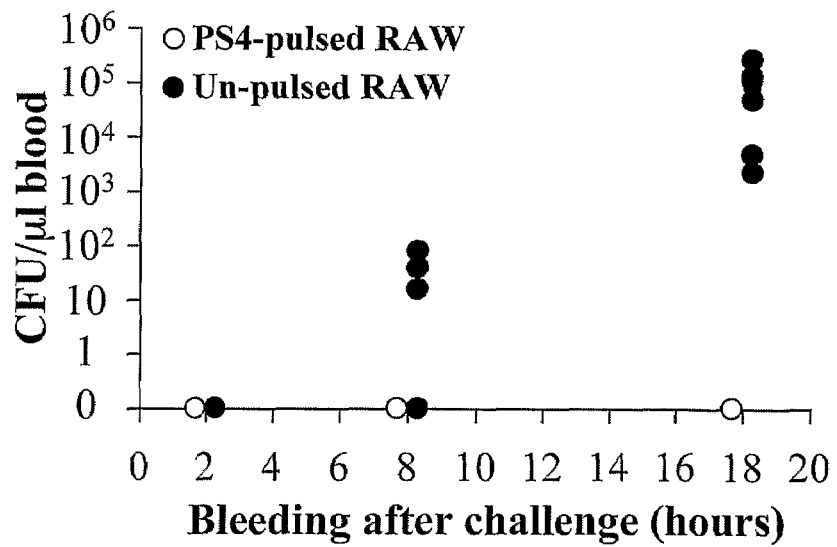

We examined the effect of cell vaccination by monitoring the bacterial counts in the blood, and not only by survival. Mice were injected with RAW cells that had been stimulated with LPS and pulsed with PS4 or with un-pulsed RAW cells, and three weeks later, the mice were challenged i.p with a lethal dose of Pn bacteria ($LD_{50} \times 100$). The numbers of CFU in the blood of the challenged mice were assayed by plating. FIG. 8B shows that the mice that had been injected with the PS4-pulsed RAW cells had undetectable numbers of bacteria in the blood 2, 8 and 18 hours after the challenge. In contrast, the mice that had been injected with un-pulsed RAW cells manifested time-dependent elevation of the CFU counts, leading to death within 24 hours. These results demonstrate that the mice protected by PS4-pulsed RAW cells rapidly eradicate the Pn challenge, and prevent the bacteria from reaching the bloodstream.

In FIG. 8B, the graph is presented in a semi-logarithmic scale and includes 6 different blood samples from each group.

Example 10

Lysed PS4-Pulsed RAW Cells Cannot Induce Resistance to Pn Challenge

Figure 8C:
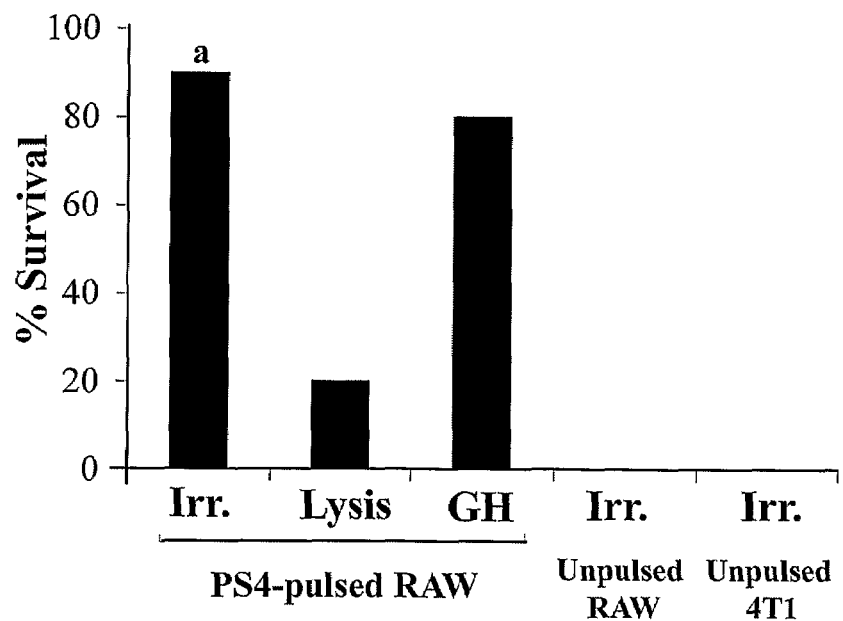

The above experiments indicated the ability of PS4-pulsed RAW cells to induce resistance to Pn challenge Are intact cells required to induce resistance, or will any cell-associated PS4 induce resistance to Pn challenge? To investigate this question, we injected mice with LPS-stimulated, PS4-pulsed RAW cells treated in three ways: following cell irradiation, lysis of the cells or gluteraldehide (GH)-fixation of the cells. We also injected mice with LPS-stimulated RAW cells un-pulsed with PS4, or with PS4-pulsed 4T1 cells, a breast cancer tumor cell line, which is a non-phagocytic cell line. FIG. 8C shows that LPS-activated macrophages effectively induced resistance to challenge when the cells were intact—either irradiated or GH-fixed. Lysed RAW cells, in contrast, were significantly less protective. Un-pulsed, but LPS-activated RAW cells, or PS4-pulsed 4T1 cells were not at all effective. These results indicate that the induction of resistance to Pn challenge is a property of RAW cells that have been activated via TLR-4 and express PS4 on their intact surface; intact cells are effective even when killed by fixation. The mere injection of PS4 with other cells or with lysed RAW cells is not sufficient.

In FIG. 8C, [a] indicates p<0.017 compared to un-pulsed RAW, lysed PS4-pulsed RAW and irradiated PS4-pulsed 4T1 cells.

Example 11

Induced Resistance Persists

Figure 8D:
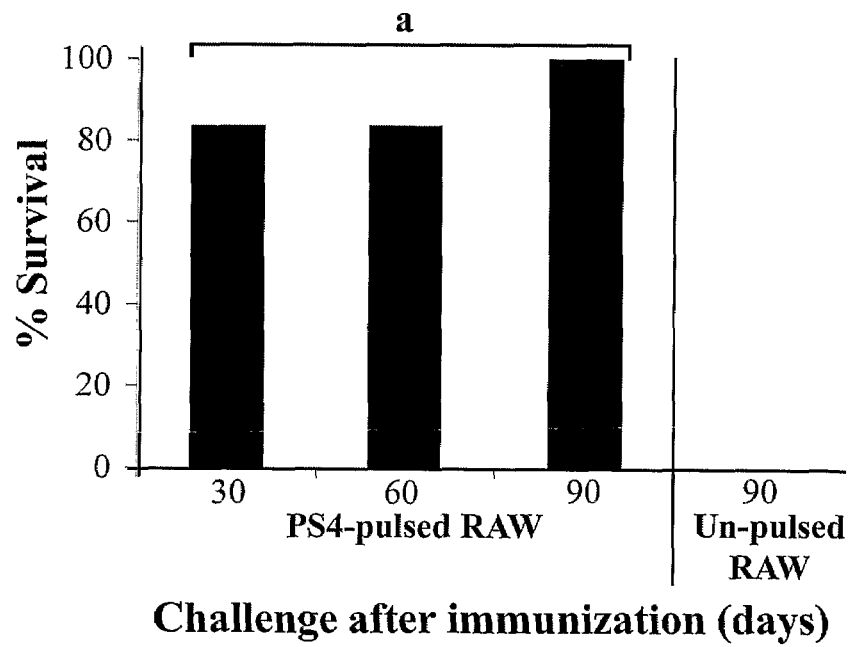

To test whether the resistance induced by LPS-activated, PS4-pulsed RAW cells persists, mice were challenged with Pn bacteria one, two or three months after injection with the treated cells. A control group of mice was injected with un-pulsed, but LPS-activated cells. FIG. 8D shows that the induced protection lasted at least three months after injection; the un-pulsed RAW cells did not induce protection.

In FIG. 8D, [a] indicates P<0.015 compared to un-pulsed RAW group.

Example 12

Protection is Ag-Specific

Next, the specificity of the immune protection was examined. To this end, mice were immunized with macrophages or dendritic cells pulsed with either pneumococcal serotype 3 CPS (PS3) or with PS4, and subsequently challenged with type 3 (Pn3) or type 4 (Pn4) pneumococci.

Figure 15A:
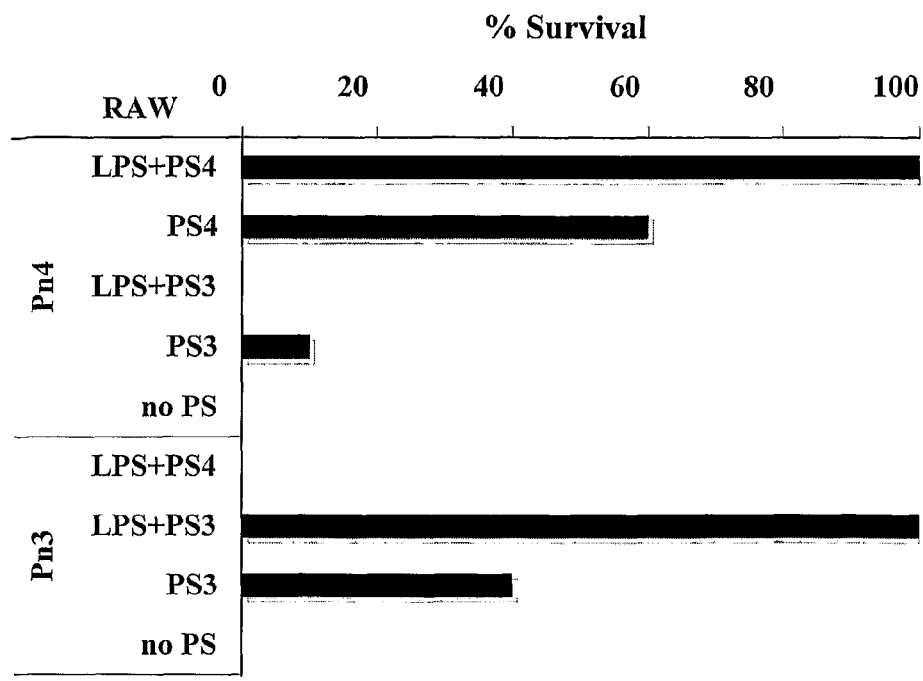

In some experiments, RAW cells were stimulated or not with LPS (5 μg/ml, 2 hrs). Then, the cells were pulsed with PS4 or PS3 (100 μg/ml, 1 hr). The cells were irradiated (5000 RAD) and injected i.p. to female BALB/c mice. Three weeks later, the mice were challenged with Pn4 or Pn3 bacteria ($LD_{50} \times 100$). As can be seen in FIG. 15A, the immunization resulted in an antigen-specific response, as protection was specific to the bacterial serotype. In FIG. 15A, P<0.02 for mice vaccinated with LPS+PS4 compared to all mice challenged with Pn4; P<0.04 for mice vaccinated with LPS+PS3 compared to all mice challenged with Pn3.

In other experiments, Bone marrow-derived dendritic cells (BMDC) were examined. To this end, BMDC were isolated as described (Ainaru et al, 2004) with modifications. Briefly, mice were sacrificed and BM was extracted from femurs and tibias by flushing the shaft with PBS. Red blood cells (RBC) were lysed in 1.66% $NH_4Cl$, and cells were seeded into non-tissue culture plates at a density of $4 \times 10^6$ cells/ml in medium (RPMI-1640, 10% FCS, $5 \times 10^{-5}$ M 2-mercapto ethanol, penicillin/streptomycin) containing 10% supernatant of B16 cells secreting GM-CSF. The medium was replenished every 3 days and the loosely adherent DC were collected at designated time points and used for further studies. To induce DC maturation, at day 8 cultures were treated with LPS (1 μg/ml) and analyzed 1 day later.

Figure 15B:
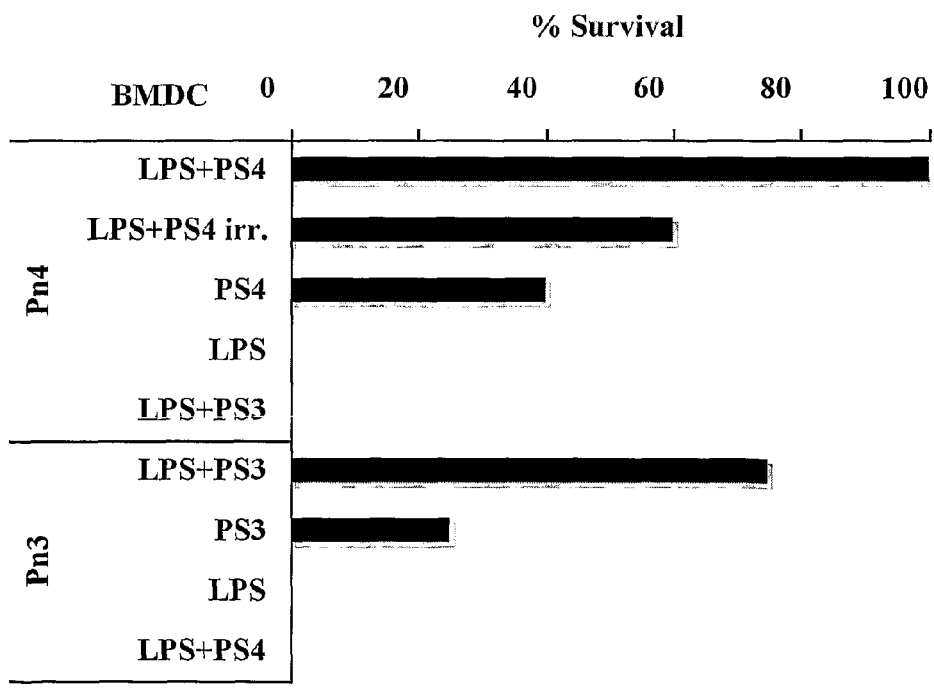

BMDC were stimulated with LPS (1 μg/ml, O/N) or not. Then, the cells were pulsed with PS4 or PS3 (100 μg/ml, 1 hr) and injected i.p to female BALB/c mice. Part of the cells was injected following irradiation (as indicated in FIG. 15B). Three weeks later, the mice were challenged with Pn4 or Pn3 bacteria ($LD_{50} \times 25000$). As can be seen in FIG. 15B, the immunization resulted in an antigen-specific response, as mice immunized with BMDC expressing PS4 or PS3 were resistant to lethal challenge by Pn4 or Pn3, respectively. In FIG. 15B, p<0.018 for LPS+PS4 compared to PS4; p<0.0045 for LPS+PS4 compared to LPS, LPS+PS3.

Example 13

Immunity by Adoptive Transfer of Splenocytes from Mice Vaccinated with PS4-Specific Cell Vaccines Splenocytes were isolated from mice vaccinated with LPS-stimulated PS4-pulsed RAW and subsequently treated ex vivo with LPS (1 μg/ml) and PS4 (10 μg/ml), or with PS4 alone or without any treatment. Splenocytes from naïve mice were used as a control. After 24 hours incubation in culture, the cells were collected and injected i.p to naïve BALB/c recipient. A day after the cell transfer, the recipient mice were challenged with Pn4 bacteria (LD50×50).

As can be seen in Table 2, splenocytes from mice vaccinated with LPS-stimulated PS4-pulsed RAW that were stimulated with LPS and PS4 ex vivo confer resistance to Pn4 challenge.

TABLE 2

| survival of recipient mice upon Pn challenge | | |
|---|---|---|
| Donor | Ex vivo treatment | Survival |
| Vaccinated | LPS 1 µg/ml + PS4 10 µg/ml | 2/2 |
|  | PS4 10 µg/ml | 0/2 |
|  | No treatment | 0/2 |
| Naïve | LPS 1 µg/ml + PS4 10 µg/ml | 0/2 |

B. Meningococcal Vaccines

Materials and Methods

Mice:

Female BALB/c mice were obtained from Harlan Olac (Bicester, UK) and were used at the age of 8 weeks unless indicated otherwise. Experiments were done according to the guidelines and under the supervision of the Animal Welfare Committee.

Peptide p458:

Peptide p458 was synthesized using an automated multiple peptide synthesizer (Abimed model AMS 422; Langenfeld, Germany), according to the company's instructions for N-α-fluorenylmethoxycarbonyl (Fmoc) synthesis. The purity of the peptide was tested by analytical reversed-phase HPLC and amino acid analysis. Peptide p458 originates from murine HSP60 at positions 458-474; its sequence is NEDQKIGIEI-IKRALKI (SEQ ID NO:2).

MnB and MnC:

MnB and MnC were prepared as previously described (Gotschlich, 1975). The Meningococcus types B or C were cultivated in modified Frantz medium (Gotschlich, 1975) in 20 litre batches until stationary growth was reached. Bacteria were removed by centrifugation at 3000 g for 10 minutes. The supernatant was collected and 1% hexadecyl-trimethylammonium bromide (Panreac Quimica S. A.; Barcelona, Spain) was added and centrifuged (10000 g, 25 minutes). CPS extraction was as follows: the pellet was dissolved in 1 litre of DDW followed by the addition of 1 litre of 2M $CaCl_2$ solution. Ethanol at 25% was then added and the mixture was incubated for 1 hour at −20° C. and then was centrifuged (20000 g, 20 minutes). The supernatant was added slowly but with agitation to an icy 80% Ethanol, incubated for an hour at 20° C. and then centrifuged (3000 g, 10 minutes). The semi-purified CPS was then dissolved in NaAc 0.1M saturated at pH=7 and vigorously mixed equally (v/v) with a phenol solution (100 g/40 mL of NaAc 0.1M saturated pH=7). The mixture was centrifuged (35000 g, 15 minutes) and the upper phase was collected. The phenol-extraction step was repeated and the resulting solution was dialyzed for 24 hours against $CaCl_2$ (0.1M). The dialyzed solution of CPS was ultracentrifuged at 100000 g for 3 hours and precipitated with Ethanol to 80%, followed by centrifugation at 3000 g for 10 min.

MnB or MnC Conjugation:

Conjugates were made using a single batch of MnC or MnB. The CPS molecules were dissolved in double distilled water (DDW) to a final concentration of 5 mg/ml and were activated (stirred continuously) with 0.1 ml of cyanogen bromide (20 mg/ml in acetone) in the presence of 30 mM triethylamine (Aldrich; Milwaukee, Wis., USA) in acetone at pH 7. The spacer 6-aminohexanoic acid (BDH Chemicals; Poole, England; 10 mg/ml in DDW) was added two minutes later to the activated CPS molecules and then incubated for 2 hours at 4° C. We then added 12 mg of water-soluble diimide: 1-(3-dimethylaminopropyl)-3-ethylcarbodiimide hydrochloride (CDI) (Aldrich; Milwaukee, Wis., USA) and 7 mg of p458 peptide to the solution. The pH was adjusted to 6 at room temperature. Four hours later, 12 mg of CDI was again added, and the mixture was incubated overnight, and then dialyzed at 4° C. against DDW. The sialic acid content was measured by the thiobarbituric acid assay (Warren, 1959). Amino acid analysis (Chemical Services, Weizmann Institute) was used to determine the amount of peptide coupled to the CPS molecules. The CPS to peptide ratios by weight of the different batches were 1.5 to 0.7 for MnB-p458 and 2 to 0.9 for MnC-p458.

Immunization:

Mice were injected s.c. on the back 3 times at 2-week intervals with the indicated dose of MnB or MnC in 0.1 ml, either conjugated or unconjugated. Unless indicated otherwise, the vaccines were emulsified in one volume of IFA per one volume of PBS containing the antigen. In the indicated experiments, the vaccines were administered in PBS alone. The dose of unconjugated p458 peptide mixed with CPS was in accordance with its relative amount in the appropriate conjugate. The administration of MnB and MnC conjugate together (MnB-p458+MnC-p458) was done with the indicated doses of CPS in 0.1 ml. The mice were bled 4 weeks after the last boost or as indicated. The blood samples were centrifuged at 14000 g for 10 minutes, and the sera were collected and stored at −20° C.

ELISA Assay:

Maxisorb 96-well plates (Nunc; Roskilde, Denmark) were coated overnight at 4° C. with 10 µg/ml of MnC or MnB in PBS. Between the different stages, the plates were washed 3 times with 0.02% Tween20 in PBS (TPBS). Each plate was blocked with 2% skim milk (DIFCO, Detroit, Mich., USA) in PBS. Serum samples were diluted 1 to 50 in 0.2% skim milk in PBS, and incubated in the well for 2 hours at 37° C. The detection of IgG Ab was done using goat anti-mouse IgG coupled to alkaline phosphatase (Jackson; West Grove, Pa., USA) diluted 1:1000, and incubated for 45 minutes at 37° C. IgM was detected using goat anti-mouse IgM coupled to alkaline phosphatase (Jackson; West Grove, Pa., USA) diluted 1:1000. IgG subtypes were detected using goat anti-mouse IgG subtypes (IgG1/2a/2b/3) coupled to alkaline phosphatase (Southern Biotechnology Association, Ink; Birmingham, Ala., USA) diluted 1:1000. The substrate solution containing 0.6 mg/ml of p-nitrophenylphosphate (Sigma; Rehovot, Israel) in diethanolamine-$H_2O$ pH 9.8 was then added. A strong color was detectable usually after 15 minutes to 1 hour of incubation. The OD was read at wavelength 405 nm ($OD_{405}$ nm).

Statistics:

Results were analyzed using Student's T Test, the Alternate Welch T Test, or the Nonparametric (Wilcoxon or Mann-Whitney) test computed using software package InState 2.01 for the Macintosh computer.

Example 12

Vaccination with Low Doses of the Conjugate Vaccine Induces IgG Abs to MnB

Mice were vaccinated 3 times with 0.2 µg, 2 µg or 2 µg CPS with the conjugate (MnB-p458), the CPS alone (Mnb) or a mixture of CPS and p458 (MnB+p458) emulsified in IFA. Sera were collected 2 weeks after the third injection and the anti-MnB IgG Ab levels were measured by ELISA. FIG. 9a shows that vaccination with the MnB-p458 conjugate at 0.2 or 2 µg per mouse was more effective than vaccination with 2 µg in the induction of IgG Abs to MnB; the effectiveness of only 0.2 µg per mouse did not differ from that of 2 µg. Further experiments were performed using the 2 µg dose per mouse.

The MnC molecule is effective in conjugate vaccines, and we compared conjugates of the MnB and MnC molecules. We tested two doses of vaccine: 2 and 20 µg CPS per mouse of the MnC-p458 conjugate or the MnC+p458 mixture, emulsified in IFA. The sera were collected and tested as described for MnB (FIG. 9b). The injection of 20 µg of MnC-p458 induced a significantly higher anti-MnC IgG Ab response than did the 2 µg dose. Hence, MnB and MnC conjugates manifest a different dose-response profile; the MnB conjugate is more effective at lower doses than the MnC.

In FIG. 9, $^a$ indicates p<0.046 compared to controls; $^b$ indicates p<0.064 compared to 2 mg MnC-p458. Each circle represents a single mouse, the horizontal line represents the mean OD and the doted line represents the change, in this and in subsequent Figures.

Example 13

Requirement for 3 Immunizations

To determine the number of immunizations required to induce IgG Abs, we injected mice 3 times with the MnB-p458 conjugate, or with MnB+p458 or MnB emulsified in IFA. The mice were bled 2 weeks after each vaccination. FIG. 10 shows that the mice produced IgG Abs to MnB after 3 immunizations with the MnB-p458 conjugate. The other vaccines failed to induce significant amounts of IgG Abs.

In FIG. 10, $^a$ indicates p<0.049 compared to MnB-p458 I and II; $^b$ indicates p<0.034 compared to MnB+p458 III and MnB III.

Example 14

MnB-p458 Induces Mainly IgG1 Abs

FIG. 11 shows that most of the IgG Abs induced in response to MnB-p458 were of the IgG1 isotype. Low levels of the IgG2a IgG2b and IgG3 isotypes were observed. Anti-MnB IgM and lower levels of IgG3 were induced both by the conjugate and by unconjugated MnB. These IgM and IgG3 Abs declined spontaneously and could not be detected after two months.

In FIG. 11, $^a$ indicates p<0.042 compared to other MnB-p458 subtypes; $^b$ indicates p<0.0005 compared to MnB Ig G1; $^c$ indicates p<0.0002 compared to MnB IgG2a; $^d$ indicates p<0.002 compared to MnB-p458 IgG2a, IgG2b and IgG3, and MnB IgG2a, IgG2b and IgG3; and $^e$ indicates p<0.028 compared to MnB IgG1, IgG2a and IgG2b.

Example 15

MnB-p458 Induces Long-Lasting Ab to MnB

Vaccines to Meningococcus type B ideally should be effective from vaccination at childhood and into adulthood. We examined the duration of IgG Abs to MnB in the sera of mice injected with the conjugate MnB-p458 or with MnB alone or mixed with the p458 peptide, emulsified in IFA. The mice were bled at 2, 6 and 14 months after the last boost (FIG. 12). Fourteen months after the last boost, at the age of about 18 months, the amount of IgG Abs was unchanged. Thus, long-lasting IgG Ab was induced by the MnB-p458 conjugate vaccine. Note, however, that not all the mice produced detectable amounts of Abs. None of the mice immunized with MnB+p458 or with MnB injected alone produced IgG Abs to MnB. In conclusion, IgG serum Abs to MnB persist in responding mice.

In FIG. 12, $^a$ indicates p<0.008 compared to controls.

Example 16

Adjuvant is Unnecessary

The adjuvant is a critical factor in vaccine design. We tested whether the p458 carrier can induce IgG Ab production without an added adjuvant; vaccination with MnB-p458 in IFA or in PBS was compared (FIG. 13a). The MnB-p458 conjugate appeared to be more effective when injected in PBS than in IFA; however, the differences were not statistically significant at this number of mice. In any case, we can conclude that IFA is not essential to the immunogenicity of MnB-p458.

We also vaccinated mice with the sub-optimal dose of 2 µg of MnC-p458 in PBS, or emulsified in IFA. A Sub-optimal dose can highlight differences in the effectiveness of vaccines that may seem to be equal at optimized doses. Surprisingly, FIG. 13b shows that mice immunized with MnC-p458 in PBS produced higher amounts of Abs to MnC. Moreover, all of the vaccinated mice produced Abs. In contrast, most of the mice injected with only 2 µg of MnC-p458 in IFA failed to produce detectable Abs (p=0.0003; see also FIG. 9). Thus, the p458 carrier seems to eliminate the need for an external adjuvant; the conjugate in PBS is sufficient for inducing an IgG immune response to the attached CPS. A vaccine that is effective when injected with no adjuvant is advantageous in human vaccination.

In FIG. 13, $^a$ indicates p<0.022 compared to MnB in PBS; $^b$ indicates p<0.0003 compared to the other MnC groups.

Example 17

Specificity of Conjugated Vaccine;
Co-Administration of Conjugated MnB and MnC
Induces Abs to Both CPSs It has been reported that the administration of conjugated MnC could induce some cross-reactive Abs to both MnC and MnB. To investigate possible cross reactivity between anti-MnB and anti-MnC Abs, we immunized mice with MnB-p458 or MnC-p458 and assayed IgG Abs binding to either MnC or MnB. FIG. 14 shows that each vaccine induced Abs that bound to the specific antigen with a 3 or 4 fold higher OD than to the other CPS. Thus, both conjugated vaccines were relatively, but not absolutely specific. We also tested whether MnB-p458 and MnC-p458 administered together might be effective in inducing IgG Abs to each CPS. The presence of MnC-p458 did not inhibit the induction of IgG Abs to MnB. Thus, there is no interference between the two conjugated vaccines.

In FIG. 14, $^a$ indicates p<0.0687 compared to MnB-p458, anti-MnB; $^b$ indicates p<0.0469 compared to MnB-p458+ MnC-p458, anti-MnB; $^c$ indicates p<0.0266 compared to MnB-p458, anti-MnC; and $^d$ indicates p<0.0409 compared to MnC-p458, anti-MnB.

Example 18

Vaccination with Ec27 Conjugates

Ec27 and Ec27h (SEQ ID NOS:5 and 6, respectively) are synthesized and conjugated to MnB, MnC or PS4 as described above. Mice are vaccinated 3 times with 0.2 µg, 2 µg or 20 µg CPS with the conjugate, the CPS alone or a mixture of CPS and peptide (Ec27 or Ec27h) emulsified in IFA. Sera are collected 2 weeks after the third injection and the anti-MnB, anti-MnC and anti-PS4 IgG Ab levels are measured by ELISA, as described above.

REFERENCES

1. Krug L M, Ragupathi G, Ng K K, Hood C, Jennings H J, Guo Z, Kris M G, Miller V, Pizzo B, Tyson L, Baez V, Livingston P O. Clin Cancer Res. 2004 Feb. 1; 10(3):916-23.
2. Lindberg A A. Vaccine 1999; 17 Suppl 2:S28-36.
3. Miller E, Salisbury D, Ramsay M. Vaccine 2001; 20 Suppl 1:S58-67.
4. Rappuoli R. Vaccine 2001; 19(17-19):2319-22.
5. Trotter C L, Andrews N J, Kaczmarski E B, Miller E, Ramsay M E. Lancet 2004; 364(9431):365-7.
6. Ricnmond P, Borrow R, Goidbiatt D, Findlow J, Martin S, Morris R, et al. J Infect Dis 2001; 183(1):160-3.
7. Devi S J, Zollinger W D, Snoy P J, Tai J Y, Costantini P, Norelli F, et al. Infect Immun 1997; 65(3):1045-52.
8. Finne J, Leinonen M, Makela P H. Lancet 1983; 2(8346): 355-7.
9. Lifely M R, Moreno C, Lindon J C. Vaccine 1987; 5(1): 11-26.
10. Morley S L, Cole M J, Ison C A, Camaraza M A, Sotolongo F, Anwar N, et al. Pediatr Infect Dis J 2001; 20(11):1054-61.
11. Robertson S E, Mayans M V, El-Husseiny A, Clemens J D, Ivanoff B. Vaccine 2001; 20(1-2):31-41.
12. Perkins B A, Jonsdottir K, Briem H, Griffiths E, Plikaytis B D, Hoiby E A, et al. J Infect Dis 1998; 177(3):683-91.
13. Haneberg B, Dalseg R, Wedege E, Hoiby E A, Haugen I L, Oftung F, et al. Infect Immun 1998; 66(4):1334-41.
14. Bartoloni A, Norelli F, Ceccarini C, Rappuoli R, Costantino P. Vaccine 1995, 13(5):463-70.
15. Fusco P C, Michon F, Tai J Y, Blake M S. J Infect Dis 1997; 175(2):364-72.
16. Qu B, Zialk M, Zuber C, Roth J. Proc Natl Acad Sci USA 1996; 93(17):8995-8.
17. Fulcuda M. Cancer Res 1996; 56(10):2237-44.
18. Komminoth P, Roth J, Saremaslani P, Matias-Guiu X, Wolfe H J, Heitz P U. Am J Surg Pathol 1994; 18(4):399-411.
19. Friedl P, Hegerfeldt Y, Tusch M. Int J Dev Biol 2004; 48(5-6):441-9.
20. Lussow et al., Immunol. Letters 1990; 25:255-264.
21. Barrios et al. Eur S of Immuol 1992; 22:1365.
22. Amir-Kroll H, Nussbaum G, Cohen I R. J Immunol 2003; 170(12):6165-71.
23. Konen-Waisman S, Cohen A, Fridkin M, Cohen I R. J Infect Dis 1999; 179(2):403-13.
24. Konen-Waisman S, Fridkin M, Cohen I R. J Immunol 1995; 154(11):5977-85.
25. Remington's Pharmaceutical Sciences, 18th ed., Mack Publishing Coiripany (1990).
26. Lussow, et al., Eur. J. Immunol. 1991; 21:2297-2302.
27. Stewart, J. M. and Young, J. D. (1963), "Solid Phase Peptide Synthesis," W.H. Freeman Co. (San Francisco).
28. Meienhofer, J (1973). "Hormonal Proteins and Peptides," vol. 2, p. 46, Academic Press (New York).
29. Schroder, G. and Lupke, K. (1965). The Peptides, vol. 1, Academic Press (New York).
30. Gotschlich E C. Monogr Allergy 1975; 9:245-58.
31. AlonsoDeVelasco, E., A. F. Verheul, J. Verhoef, and H. Snippe. *Microbiol. Rev* 1995; 59:591.
32. Lesinsli, G. B., and M. A. Westerink. *J Microbiol Methods* 2001; 47:135.
33. Cohen-Sfady, M., G. Nussbaum, M. Pevsner-Fischer, F. Mor, P. Carmi, A. Zanin-Zhorov, O. Lider, and I. R. Cohen. *J Immunol* 2005; 175:3594.
34. Rouvio 0, Dvorkin T, Amir-Kroll H, Atias D, Cohen I R, Rager-Zisman B, Porgador A. Vaccine 2005; 23(27):3508-18.
35. Sambrook et al., Molecular Cloning: A Laboratory Manual. 3rd edn., 2001, Cold Spring Harbor Laboratory Press.
36. Robbins J B, Schneerson R. Bull Eur Physiopathol Respir 1983; 19(2):215-26.
37. Kohn, J. and M. Wilchek. Biochem Biophys Res Commun 1982; 107(3): 878-84.
38. Schneerson, R., O. Barrera, et al. J Exp Med 1980; 152(2): 361-76.
39. Vinogradov E, Fridrich E, MacLean L L, Perry M B, Petersen B O, Duus J O, Whitfield C. J Biol. Chem. 2002; 277(28):25070-81.
40. Pizza M, Scarlato V, Masignani V, Giuliani M M, Arico B, Comanducci M, Jennings G T, Baldi L, Bartolini E, Capecchi B, Galeotti C L, Luzzi E, Manetti R, Marchetti E, Mora M, Nuti S, Ratti G, Santini L, Savino S, Scarselli M, Storni E, Zuo P, Broeker M, Hundt E, Knapp B, Blair E, Mason T, Tettelin H, Hood D W, Jeffries A C, Saunders N J, Granoff D M, Venter J C, Moxon E R, Grandi G, Rappuoli R. Science. 2000; 287(5459):1816-20.
41. Feng L, Perepelov A V, Zhao G, Shevelev S D, Wang Q, Senchenlkova S N, Shashikov A S, Geng Y, Reeves P R, Knirel Y A, Wang L. Microbiology. 2007; 153(Pt 1):139-47.
42. Burnie J P, Matthews R C, Carter T, Beaulieu E, Donohoe M, Chapman C, Williamson P, Hodgetts S J. Infect Immun. 2000; 68(6):3200-9.
43. Carlin N I, Lindberg A A. Infect Immun. 1987; 55(6): 1412-20.
44. von Eiff C, Taylor K L, Mellmann A, Fattom A I, Friedrich A W, Peters G, Becker K. Diagn Microbiol Infect Dis. 2007.
45. Henikoff S, Henikoff J G. Proc Natl Acad Sci USA. 1992 Nov. 15; 89(22):10915-9.
46. Ainaru O et al EMBO J. 2004 Feb. 25; 23(4):969-79

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A composition containing an immunogenic conjugate, the conjugate comprising an antigen covalently attached to HSP60-derived peptide sequences selected from the group consisting of:

(a) NEDQKIGIEIIKRTLKI, (p458h; SEQ ID NO: 1)
(b) NEDQKIGIEIIKRALKI, (p458; SEQ ID NO: 2)
(c) EGDEA TGANIVKV ALEA, (p458mt; SEQ ID NO: 3)
(d) NEDQNVGIKV ALRAMEA, (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;
wherein the conjugate comprises a weight ratio of HSP60-derived peptide to antigen in excess of 1:1 (w/w);
with the proviso that said antigen is other than the capsular polysaccharide (CPS) Vi of *Salmonella typhi*.

2. The composition of claim 1, comprising an antigen covalently attached to a multimeric carrier, in which the carrier comprises a plurality of peptide units comprising HSP60-derived sequences selected from the group of peptides consisting of:

(a) NEDQKIGIEIIKRTLKI, (p458h; SEQ ID NO: 1)
(b) NEDQKIGIEIIKRALKI, (p458; SEQ ID NO: 2)
(c) EGDEATGANIVKVALEA, (p458mt; SEQ ID NO: 3)
(d) NEDQNVGIKVALRAMEA, (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the antigen is a bacterial capsular polysaccharide (CPS) other than the CPS Vi of *Salmonella typhi*; and wherein said conjugate has a peptide/polysaccharide ratio (w/w) of at least 1:1.

3. The composition of claim 1, wherein the antigen is a polysaccharide or oligosaccharide.

4. The composition of claim 3, wherein said antigen is a homopolymer of sialic acid selected from an $\alpha(2\text{-}8)$ sialic acid homopolymer and an $\alpha(2\text{-}9)$ sialic acid homopolymer.

5. An immunogenic conjugate comprising an antigen covalently attached to a multimeric carrier, in which the carrier comprises a plurality of peptide units comprising heat shock protein 60 (HSP60)-derived sequences selected from the group of peptides consisting of:

(a) NEDQKIGIEIIKRTLKI, (p458h; SEQ ID NO: 1)
(b) NEDQKIGIEIIKRALKI, (p458; SEQ ID NO: 2)
(c) EGDEATGANIVKVALEA, (p458mt; SEQ ID NO: 3)
(d) NEDQNVGIKVALRAMEA, (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;
wherein the conjugate comprises at least about 30 peptide units per antigen molecule;
with the proviso that said antigen is other than the capsular polysaccharide (CPS) Vi of *Salmonella typhi*.

6. The conjugate of claim 5, wherein said conjugate comprises between about 50 and about 200 peptide units per antigen molecule.

7. The conjugate of claim 5, wherein said conjugate comprises at least one analog of p458h (SEQ ID NO: 1): 458NEDQKIGIEIIKRTLKI474 in which the residue E459 is either E or D; the residue D460 is either D or E; the residue K462 is either K or R or ornithine (Orn); the residue I463 is either I or L, V, M, F, norleucine (Nle) or norvaline (Nva); the residue I465 is either I or L, V, M, F, Nle or Nva; the residue E466 is either E or D; the residue I467 is either I or L, V, M, F, Nle or Nva; the residue I468 is either I or L, V, M, F, Nle or Nva; the residue K469 is either K or R or Orn; the residue R470 is either R, K or Orn; the residue L472 in either L or I, V, M, F, Nle or Nva; the residue K473 is either K or R or Orn; and the residue I474 is either I or L, V, M, F, Nle or Nva.

8. The conjugate of claim 5, wherein the antigen is selected from the group consisting of polypeptides, peptides, peptide derivatives, saccharides, lipoproteins, glycolipids and antibodies.

9. The conjugate of claim 5, wherein the antigen is selected from the group consisting of antigens derived from *Streptococcus pneumoniae, Neisseria meningitidis, Staphylococcus aureus, Shigella flexneri, Klebsiella pneumoniae* and enterotoxigenic *Escherichia coli*.

10. The conjugate of claim 8, wherein said antigen is a bacterial CPS or a fragment thereof.

11. The conjugate of claim 10, wherein the antigen is a *Streptococcus pneumoniae* (*S. pneumoniae*) CPS.

12. The conjugate of claim 11, wherein the CPS is selected from the group consisting of CPS derived from *S. pneumoniae* serotypes [as detailed in Table 1] 1, 2, 3, 4, 5, 8, 9N, 12F, 14, 17F, 19F, 20, 22F, 23F, 25, 6B, 10A, 11A, 7F, 15B, 18C, 19A, 9V and 33F (Danish designation).

13. The conjugate of claim 12, wherein the *S. pneumoniae* CPS is a *S. pneumoniae* CPS type 4 (PS4).

14. The conjugate of claim 10, wherein the antigen is a *Neisseria meningitidis* (*N. meningitidis*) CPS.

15. The conjugate of claim 14, wherein the CPS is selected from the group consisting of CPS derived from *N. meningitidis* Group A, B, C, W-135 and Y.

16. The conjugate of claim 15, wherein said *N. meningitidis* CPS is a *N. meningitidis* group B CPS (MnB).

17. The conjugate of claim 15, wherein said *N. meningitidis* CPS is a *N. meningitidis* group C CPS (MnC).

18. The conjugate of claim 10, wherein said conjugate has a peptide/polysaccharide ratio (w/w) of at least 1:1, of at least 2:1, or of between about 1.5:1 and 6:1.

19. A composition comprising at least one immunogenic conjugate according to claim 5 and a pharmaceutically acceptable carrier, excipient or diluent.

20. The composition of claim 19, the composition comprising between about 0.1 and about 1000 µg of said conjugate, between about 0.1 and about 100 µg of said immunogenic conjugate or between about 0.2 and about 25 µg of said immunogenic conjugate wherein the antigen is MnB.

21. The composition of claim 20, wherein said conjugate comprises about 30 to about 200 peptide units per antigen molecule or about 40 to about 100 peptide units per antigen molecule.

22. The composition of claim 20, further comprising a second immunogenic conjugate, wherein the second conjugate comprises an antigen covalently attached to a multimeric carrier, in which the antigen is a *Neisseria meningitides* group C CPS (MnC) and the carrier comprises a plurality of peptide units comprising heat shock protein 60 (HSP60)-derived sequences selected from the group of peptides consisting of:

(a) NEDQKIGIEIIKRTLKI,   (p458h; SEQ ID NO: 1)
(b) NEDQKIGIEIIKRALKI,   (p458; SEQ ID NO: 2)
(c) EGDEATGANIVKVALEA,   (p458mt; SEQ ID NO: 3)
(d) NEDQNVGIKVALRAMEA,   (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the conjugate comprises at least about 30 peptide units per antigen molecule;

with the proviso that said antigen is other than the capsular polysaccharide (CPS) Vi of *Salmonella typhi*.

23. The composition of claim 22, wherein said second conjugate comprises about 30 to about 200 peptide units per antigen molecule or about 40 to about 100 peptide units per antigen molecule, or wherein said composition comprises between about 10 and about 1000 µg of the second conjugate, between about 20 and about 500 µg of the second conjugate or between about 40 and about 250 µg of the second conjugate.

24. A method for enhancing the immunogenicity of an antigen comprising conjugating the antigen to a plurality of peptide units comprising HSP60-derived sequences, in which each peptide unit is selected from the group of peptides consisting of:

(a) NEDQKIGIEIIKRTLKI,   (p458h; SEQ ID NO: 1)
(b) NEDQKIGIEIIKRALKI,   (p458; SEQ ID NO: 2)
(c) EGDEATGANIVKVALEA,   (p458mt; SEQ ID NO: 3)
(d) NEDQNVGIKVALRAMEA,   (p458e; SEQ ID NO: 4)

(e) an analog or derivative of p458h (SEQ ID NO: 1) that has at least 70% of the electric and hydrophilicity/hydrophobicity characteristic of human HSP60 from position 458 to position 474, said peptide, analog or derivative being capable of increasing substantially the immunogenicity of the antigen when the conjugate is administered in vivo;

wherein the antigen is conjugated to at least about 30 peptide units;

with the proviso that said antigen is other than the capsular polysaccharide (CPS) Vi of *Salmonella typhi*.

25. A method for immunizing a subject in need thereof, comprising administering to the subject an effective amount of a vaccine composition according to claim 1.

26. A method for immunizing a subject in need thereof, comprising administering to the subject an effective amount of a composition according to claim 19.

* * * * *

SEQUENCE LISTING

<160> NUMBER OF SEQ ID NOS: 7

<210> SEQ ID NO 1
<211> LENGTH: 17
<212> TYPE: PRT
<213> ORGANISM: Artificial Sequence

```
<220> FEATURE:
<223> OTHER INFORMATION: synthetic peptide

<400> SEQUENCE: 1

Asn Glu Asp Gln Lys Ile Gly Ile Glu Ile Ile Lys Arg Thr Leu Lys
1               5                   10                  15

Ile

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Asn Glu Asp Gln Lys Ile Gly Ile Glu Ile Ile Lys Arg Ala Leu Lys
1               5                   10                  15

Ile

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Glu Gly Asp Glu Ala Thr Gly Ala Asn Ile Val Lys Val Ala Leu Glu
1               5                   10                  15

Ala

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Asn Glu Asp Gln Asn Val Gly Ile Lys Val Ala Leu Arg Ala Met Glu
1               5                   10                  15

Ala

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Lys Lys Ala Arg Val Glu Asp Ala Leu His Ala Thr Arg Ala Ala Val
1               5                   10                  15

Glu Glu Gly Val
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6
```

```
Lys Lys Asp Arg Val Thr Asp Ala Leu Asn Ala Thr Arg Ala Ala Val
1               5                   10                  15

Glu Glu Gly Ile
            20

<210> SEQ ID NO 7
<211> LENGTH: 34
<212> TYPE: PRT
<213> ORGANISM: Artificial Sequence
<220> FEATURE:
<223> OTHER INFORMATION: Synthetic peptide

<400> SEQUENCE: 7

Asn Glu Asp Gln Lys Ile Gly Ile Glu Ile Ile Lys Arg Thr Leu Lys
1               5                   10                  15

Ile Asn Glu Asp Gln Lys Ile Gly Ile Glu Ile Ile Lys Arg Thr Leu
            20                  25                  30

Lys Ile
```